US008140170B2

United States Patent
Rezai et al.

(10) Patent No.: US 8,140,170 B2
(45) Date of Patent: Mar. 20, 2012

(54) METHOD AND APPARATUS FOR RENAL NEUROMODULATION

(75) Inventors: Ali R. Rezai, Shaker Heights, OH (US); Roy K. Greenberg, Bratenahl, OH (US); Milind Deogaonkar, Broadview Heights, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 712 days.

(21) Appl. No.: 12/101,452

(22) Filed: Apr. 11, 2008

(65) Prior Publication Data

US 2009/0024195 A1    Jan. 22, 2009

Related U.S. Application Data

(63) Continuation-in-part of application No. 11/641,331, filed on Dec. 19, 2006, and a continuation-in-part of application No. 11/222,766, filed on Sep. 12, 2005, now abandoned.

(60) Provisional application No. 60/922,965, filed on Apr. 11, 2007.

(51) Int. Cl.
*A61N 1/05* (2006.01)

(52) U.S. Cl. .................. 607/116; 607/1; 607/2; 607/40; 607/41; 607/115; 607/118

(58) Field of Classification Search .................. 607/1–2, 607/40–41, 115–116, 118
See application file for complete search history.

(56) References Cited

U.S. PATENT DOCUMENTS

| 5,716,377 | A | 2/1998 | Rise et al. |
|---|---|---|---|
| 6,827,735 | B2 | 12/2004 | Greenberg |
| 7,162,303 | B2 | 1/2007 | Levin et al. |
| 2002/0138109 | A1 | 9/2002 | Keogh et al. |
| 2003/0216792 | A1 | 11/2003 | Levin et al. |
| 2004/0249416 | A1 | 12/2004 | Yun et al. |
| 2005/0021092 | A1 | 1/2005 | Yun et al. |
| 2005/0234523 | A1 | 10/2005 | Levin et al. |
| 2005/0288730 | A1 | 12/2005 | Deem et al. |
| 2006/0025821 | A1 | 2/2006 | Gelfand et al. |
| 2006/0041277 | A1 | 2/2006 | Deem et al. |
| 2006/0085046 | A1 | 4/2006 | Rezai et al. |
| 2006/0116720 | A1 | 6/2006 | Knoblich |
| 2006/0142801 | A1 | 6/2006 | Demarais et al. |
| 2006/0206149 | A1 | 9/2006 | Yun |
| 2006/0206150 | A1 | 9/2006 | Demarais et al. |
| 2006/0212076 | A1 | 9/2006 | Demarais et al. |
| 2006/0212078 | A1 | 9/2006 | Demarais et al. |
| 2006/0235474 | A1 | 10/2006 | Demarais |
| 2006/0247761 | A1 | 11/2006 | Greenberg et al. |
| 2006/0265014 | A1 | 11/2006 | Demarais et al. |
| 2006/0265015 | A1 | 11/2006 | Demarais et al. |
| 2006/0276852 | A1 | 12/2006 | Demarais et al. |
| 2007/0060972 | A1 | 3/2007 | Kieval et al. |
| 2007/0066929 | A1 | 3/2007 | Ferren et al. |
| 2007/0066957 | A1 | 3/2007 | Demarais et al. |
| 2007/0142879 | A1 | 6/2007 | Greenberg et al. |
| 2008/0208305 | A1 | 8/2008 | Rezai et al. |

*Primary Examiner* — Carl H Layno
*Assistant Examiner* — Deborah Malamud
(74) *Attorney, Agent, or Firm* — Tarolli, Sundheim, Covell & Tummino LLP

(57) ABSTRACT

An apparatus for renal neuromodulation includes an expandable support member having a main body portion for engaging a wall of a blood vessel proximate a renal vasculature and at least one electrode connected with the main body portion. The at least one electrode is arranged to selectively deliver electric current to a desired location where modulation of the sympathetic nervous system is effective to alter renal function. The apparatus further includes an insulative material attached to at least a portion of the main body portion for isolating blood flow through the vessel from the electric current delivered by the at least one electrode.

83 Claims, 15 Drawing Sheets

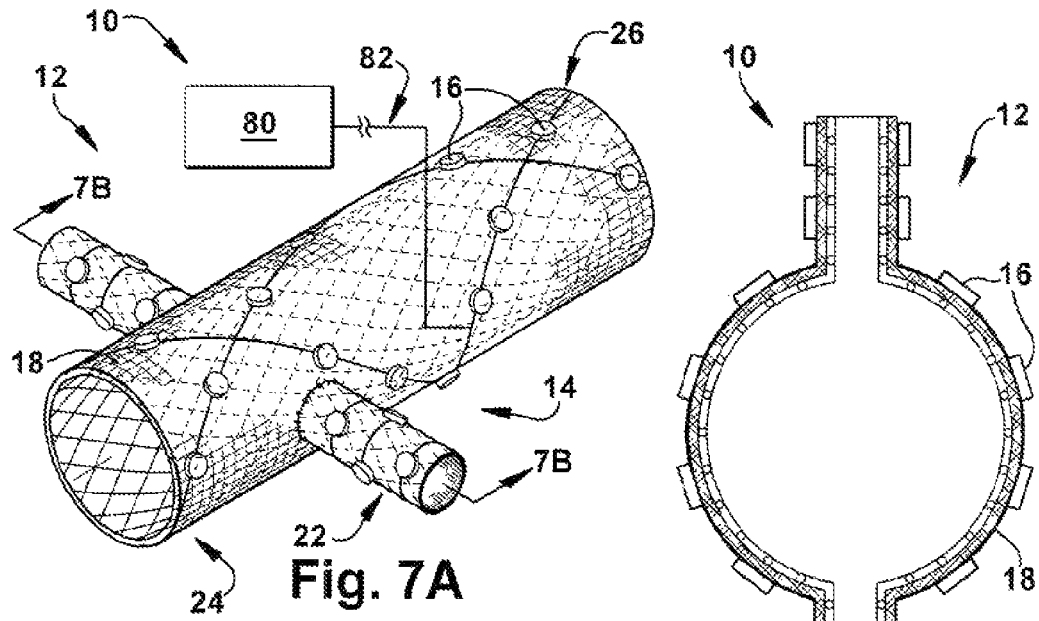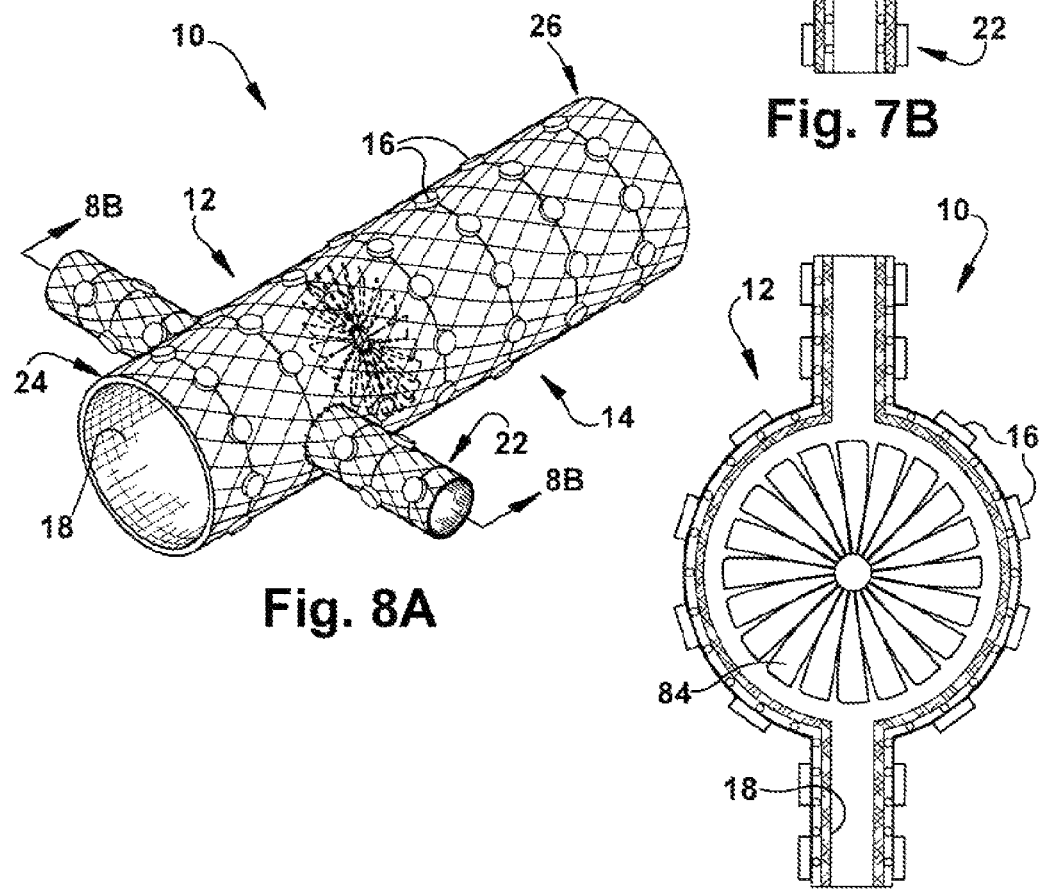

METHOD AND APPARATUS FOR RENAL NEUROMODULATION

RELATED APPLICATIONS

This applications claims priority from U.S. Provisional Patent Application Ser. No. 60/922,965, filed Apr. 11, 2007, it is a continuation in part of U.S. patent application Ser. No. 11/641,331, filed Dec. 19, 2006, and a continuation in part of U.S. patent application Ser. No. 11/222,766, filed Sep. 12, 2005, now abandoned. The subject matter of the aforementioned applications is incorporated by reference in their entireties.

TECHNICAL FIELD

The present invention relates generally to renal neuromodulation, and more particularly to methods and apparatus for achieving renal neuromodulation via an implantable device capable of delivering an electric current to a desired intravascular location.

BACKGROUND OF THE INVENTION

The kidneys are a pair of organs that lie in the back of the abdomen on each side of the vertebral column. The kidneys play an important regulatory role in maintaining the homeostatic balance of the body. For example, the kidneys eliminate foreign chemicals from the body, regulate inorganic substances and extracellular fluid, and function as endocrine glands, secreting hormonal substances like renin and erythropoietin.

The main functions of the kidneys are maintaining the water balance of the body and controlling metabolic homeostasis. Healthy kidneys regulate the amount of fluid in the body by making urine more or less concentrated, thus either reabsorbing or excreting more fluid, respectively. Urine production in the kidneys is regulated in part through autoregulation, which involves reflexive changes in the diameters of the arterioles supplying the nephrons, thereby altering blood flow and filtration rates. Both hormonal and neural mechanisms can supplement or adjust the local responses.

The kidneys and ureters are innervated by the renal nerves. Most of the nerve fibers involved are sympathetic postganglionic fibers from the superior mesenteric ganglion. A renal nerve enters each kidney at the hilus and follows the branches of the renal artery to reach individual nephrons. Known functions of sympathetic innervation include: (1) regulation of renal blood flow and pressure; (2) stimulation of renin release; and (3) direct stimulation of water and sodium ion resorption.

A variety of methods are currently used to treat kidney disease and conditions associated with kidney disease. For example, pharmacological compositions, such as FERRLECIT (iron gluconate) and VENOFER (iron sucrose), dialysis, and surgical intervention, such as kidney transplantation, are all used. Another method used to treat kidney disease and conditions associated with kidney disease involves electrostimulation of the renal nerves. Such electrostimulation methods, however, are often non-specific and offer only short-term symptomatic relief.

SUMMARY OF THE INVENTION

In one aspect of the present invention, an apparatus for renal neuromodulation comprises an expandable support member having a main body portion for engaging a wall of a blood vessel proximate a renal vasculature, and at least one electrode connected with the main body portion. The at least one electrode is arranged to selectively deliver electric current to a desired location where modulation of the sympathetic nervous system (SNS) is effective to alter renal function. The apparatus further includes an insulative material attached to at least a portion of the main body portion for isolating blood flow through the vessel from the electric current delivered by the at least one electrode.

In another aspect of the present invention, an apparatus for renal neuromodulation comprises an expandable support member for engaging a wall of a blood vessel proximate a renal vasculature. The expandable support member includes a main body portion having at least one fenestration and at least one branch member for engaging a wall of a blood vessel in the renal vasculature. The at least one branch member includes first and second end portions. The first end portion is anastomosed with the at least one fenestration. The apparatus further includes at least one electrode connected with the expandable support member arranged to selectively deliver electric current to a desired location where modulation of the SNS is effective to alter renal function. The apparatus also includes an insulative material attached to at least a portion of the expandable support member for isolating blood flow through the vessel from the electric current delivered by the at least one electrode.

In another aspect of the present invention, an apparatus for renal neuromodulation comprises an expandable support member having a main body portion for engaging a wall of a blood vessel proximate a renal vasculature, and at least one electrode connected with the main body portion arranged to selectively deliver electric current to a desired location where modulation of the SNS is effective to alter renal function. The apparatus further includes at least one wireless module capable of receiving electrical energy for delivery to the at least one electrode.

In another aspect of the present invention, a method for renal neuromodulation is provided. One step of the method includes providing an expandable support member having a main body portion for engaging a wall of a blood vessel proximate a renal vasculature. The expandable support member includes at least one electrode connected with the main body portion arranged to selectively deliver electric current to a desired location, and an insulative material attached to at least a portion of the main body portion for isolating blood flow through the vessel from the electric current delivered by the at least one electrode. The main body portion is implanted intravascularly so that the main body portion is proximate a renal vasculature and at least one electrode is positioned substantially adjacent a desired location where modulation of the SNS is effective to alter renal function. Electric current is then delivered to the at least one electrode to effect a change in the SNS.

In another aspect of the present invention, a method for renal neuromodulation is provided. One step of the method includes providing an expandable support member for engaging a wall of a blood vessel proximate a renal vasculature. The expandable support member includes a main body portion having at least one fenestration and at least one branch member having first and second end portions. The first end portion is anastomosed with the at least one fenestration. The expandable support member further includes at least one electrode connected with the expandable support member arranged to selectively deliver electric current to a desired location, and an insulative material attached to at least a portion of the expandable support member for isolating blood flow through the vessel from the electric current delivered by the at least one electrode. The main body portion is implanted intravascularly so that the main body portion is proximate a renal vasculature and at least one electrode is positioned substantially adjacent a desired location where modulation of the SNS is effective to alter renal function. The at least one branch member is then deployed such that the at least one branch member is positioned in the renal vasculature and at least one electrode is positioned substantially adjacent a desired location where modulation of the SNS is possible. Electric current is then delivered to one or both of the at least one electrode to effect a change in the SNS.

In another aspect of the present invention, a method for renal neuromodulation is provided. One step of the method includes providing an expandable support member having a cuff-like configuration and comprising a main body portion. The main body portion includes a lumen for engaging an extravascular wall of a blood vessel comprising a portion of a renal vasculature. The expandable support member also includes at least one electrode connected with the main body portion and being arranged to selectively deliver electric current to a desired location, and an insulative material attached to at least a portion of the main body portion. The main body portion is implanted extravascularly so that the main body portion is in direct contact with a portion of the renal vasculature and at least one electrode is positioned substantially adjacent a desired location where modulation of the SNS is effective to alter renal function. Electric current is then delivered to the at least one electrode to effect a change in the SNS.

BRIEF DESCRIPTION OF THE DRAWINGS

The foregoing and other features of the present invention will become apparent to those skilled in the art to which the present invention relates upon reading the following description with reference to the accompanying drawings, in which:

FIG. 7A is a perspective view showing an alternative embodiment of the apparatus shown in FIG. 1;

FIG. 7B is a schematic sectional view taken along line 7-7 in FIG. 7A;

FIG. 8A is a perspective view showing another alternative embodiment of the apparatus shown in FIG. 1;

FIG. 8B is a schematic sectional view taken along line 8-8 in FIG. 8A;

DETAILED DESCRIPTION

Figure 1:
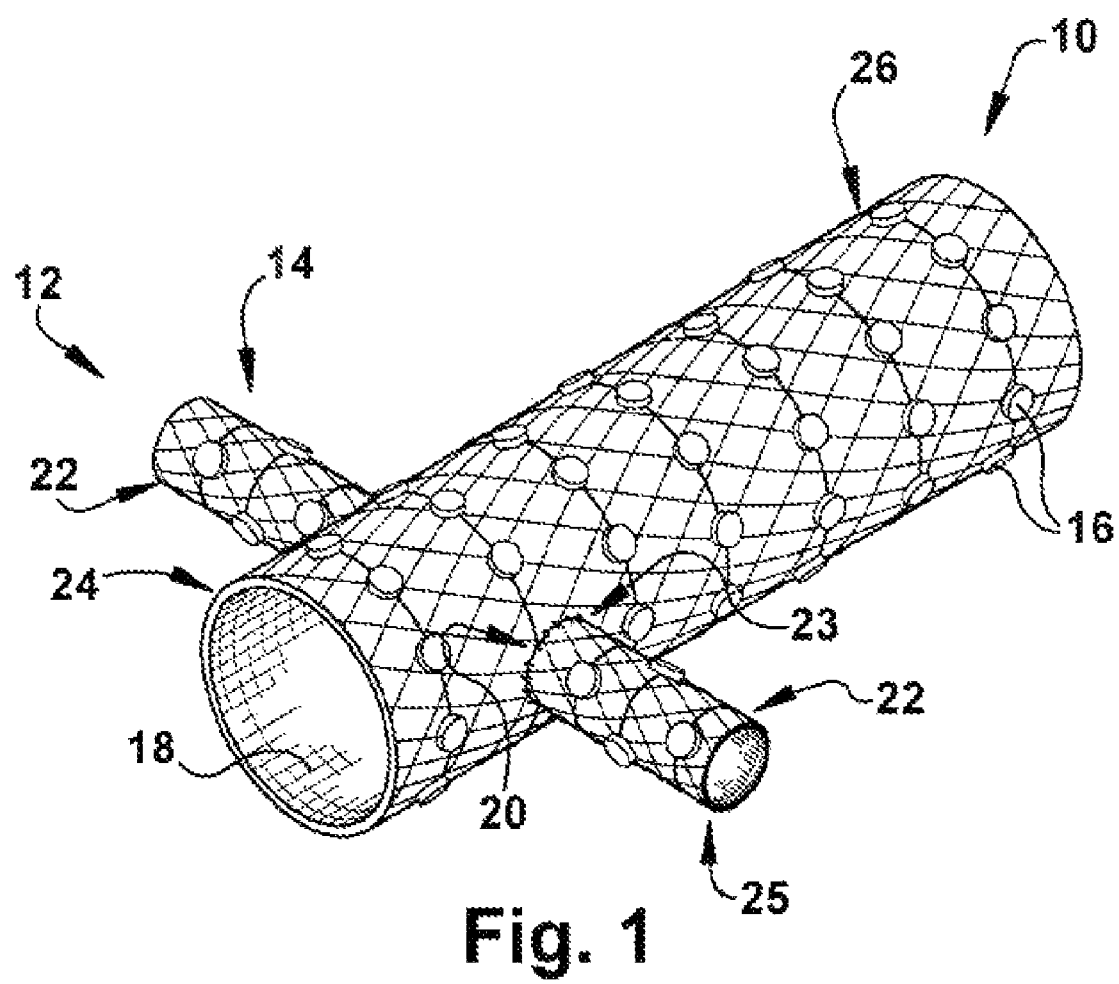
FIG. 1 is a perspective view of an apparatus for insertion into a blood vessel and for renal neuromodulation constructed in accordance with the present invention.
Figure 4:
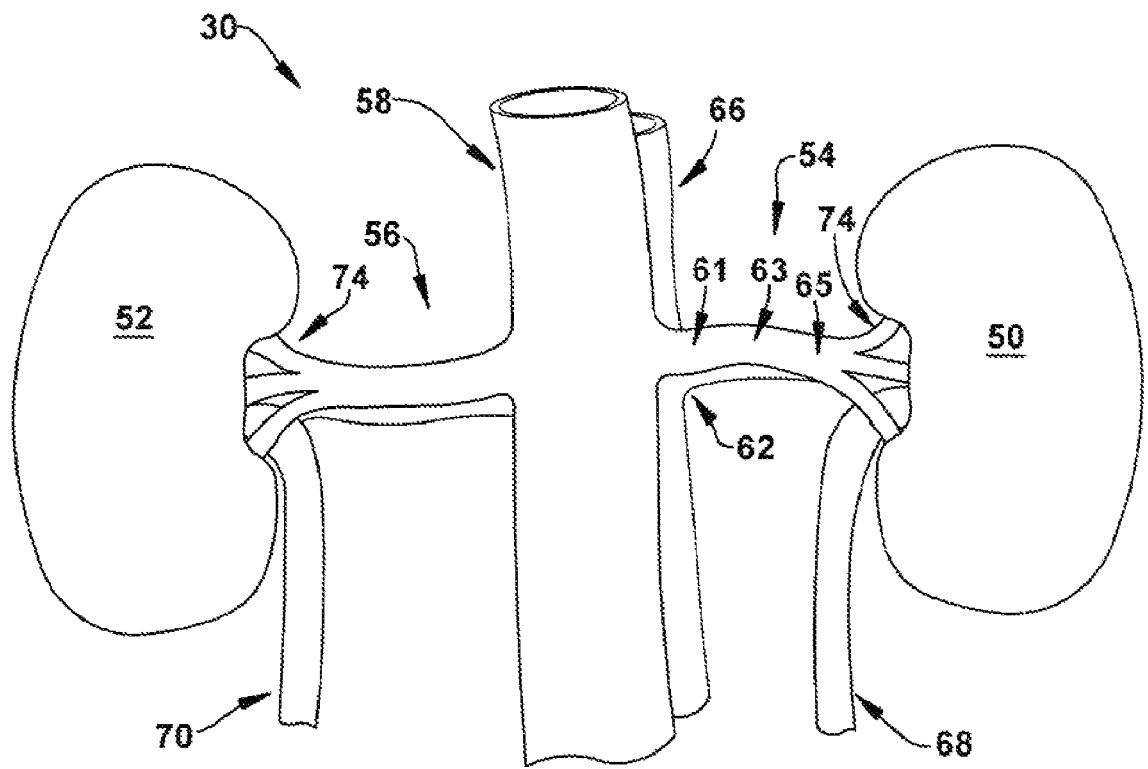
FIG. 4 is a schematic view illustrating human renal anatomy.

The present invention relates generally to renal neuromodulation, and more particularly to methods and apparatus for achieving renal neuromodulation via an implantable device capable of delivering an electric current to a desired intravascular location. As representative of the present invention, FIG. 1 illustrates an apparatus 10 for renal neuromodulation. The apparatus 10 comprises an expandable support member 12 having a main body portion 14 for engaging a wall of a blood vessel proximate a renal vasculature 30 (FIG. 4). The expandable support member 12 (FIG. 1) includes at least one electrode 16 and an insulative material 18 attached to at least a portion of the expandable support member. The main body portion 14 includes at least one fenestration 20 and at least one branch member 22 anastomosed with the at least one fenestration.

Unless otherwise defined, all technical terms used herein have the same meaning as commonly understood by one of ordinary skill in the art to which the present invention pertains.

In the context of the present invention, the term "renal vasculature" refers to the kidneys and their associated anatomical structures, such as the renal arteries, the renal veins, and the ureters.

As used herein, the term "sympathetic nervous system" or "SNS" refers to the part of the autonomic nervous system originating in the thoracic and lumbar regions of the spinal cord that generally inhibits or opposes the physiological effects of the parasympathetic nervous system (PNS).

As used herein, the term "desired location" refers to a desired anatomical location at which the present invention may be positioned. The desired location can comprise a variety of anatomical locations, including intraluminal and extraluminal locations innervated by at least one nerve. For example, the desired location can comprise an intravascular or extravascular location innervated by at least one nerve. Examples of desired locations according to the present invention include, but are not limited to, the renal sinus, the renal arteries, the intraabdominal artery, the smaller arteries and arterioles of the kidneys, such as the segmental arteries, the lobar arteries, the interlobar artery, the arcuate arteries, the afferent arterioles, and the glomerulus, the left and right ureters, the renal ganglia, such as the celiac ganglia, the superior mesenteric ganglion, the left and right aorticorenal ganglia, the inferior mesenteric ganglion, and the efferent fibers emanating therefrom. Desired locations contemplated by the present invention are also illustrated in FIGS. 2-5 and FIGS. 14-20, and are described in further detail below.

As used herein, the term "anastomosis" refers to a connection between two lumens that puts the lumens in fluid communication with each other. "Anastomosing" refers to the process of forming an anastomosis.

As used herein, the terms "renal disease" or "renal disorder" refer to any disease or disorder afflicting the renal vasculature and/or renal physiology. Renal disease may be marked by decline in kidney function over time (i.e., a chronic condition), as well as acute damage to the kidneys resulting in loss of renal function. Renal disease can result from a primary pathology of the kidneys (e.g., injury to the glomerulus or tubule) or another organ (e.g., pancreas) which adversely affects the ability of the kidneys to perform biological functions (e.g., retain protein). Thus, renal disease can be the direct or indirect effect of disease. Examples of a renal disease as a result or consequence of an indirect effect on the kidneys is kidney disease as a consequence of diabetes or systemic lupus. Other examples of renal disease include, but are not limited to, nephritis (acute and chronic), nephropathy, hyperfiltration, mild microalbuminuria, clinical albuminuria, kidney failure, polycystic kidney disease, chronic renal insufficiency, chronic or acute renal failure, end-stage renal disease, acute nephritic syndrome, analgesic nephropathy, atheroembolic renal disease, Goodpasture's syndrome, interstitial nephritis, kidney cancer, kidney infection, kidney stones, membranoproliferative glomerulonephritis (GN) I, membranoproliferative GN II, membranous nephropathy, necrotizing GN, nephrocalcinosis, post-streptococcal GN, reflux nephropathy, renal artery embolism, renal artery stenosis, renal papillary necrosis, renal tubular acidosis (types I and II), renal underperfusion, renal vein thrombosis, and disorders or diseases associated with renal disease, such as chronic or acute congestive heart failure and hypertension (e.g., chronic hypertension).

As used herein, the term "renal excretion" refers to the removal of organic wastes from bodily fluids by the kidneys.

As used herein, the term "renal elimination" refers to the discharge of waste products via the kidneys and/or ureters.

As used herein, the term "homeostatic regulation" refers to the regulation or control of blood plasma volume and solute concentration by the kidneys. Examples of homeostatic regulation include: (1) regulation of blood volume and pressure by, for example, adjusting volume of water lost in the urine and releasing erythropoietin and renin); (2) regulating plasma ion concentrations (e.g., sodium, potassium, chloride ions, and calcium ion levels) by controlling the quantities lost in the urine and the synthesis of calcitrol; (3) stabilizing blood pH by controlling loss of hydrogen and bicarbonate ions in the urine; (4) conserving valuable nutrients by preventing their excretion; and (5) assisting the liver with detoxification.

Figure 2:
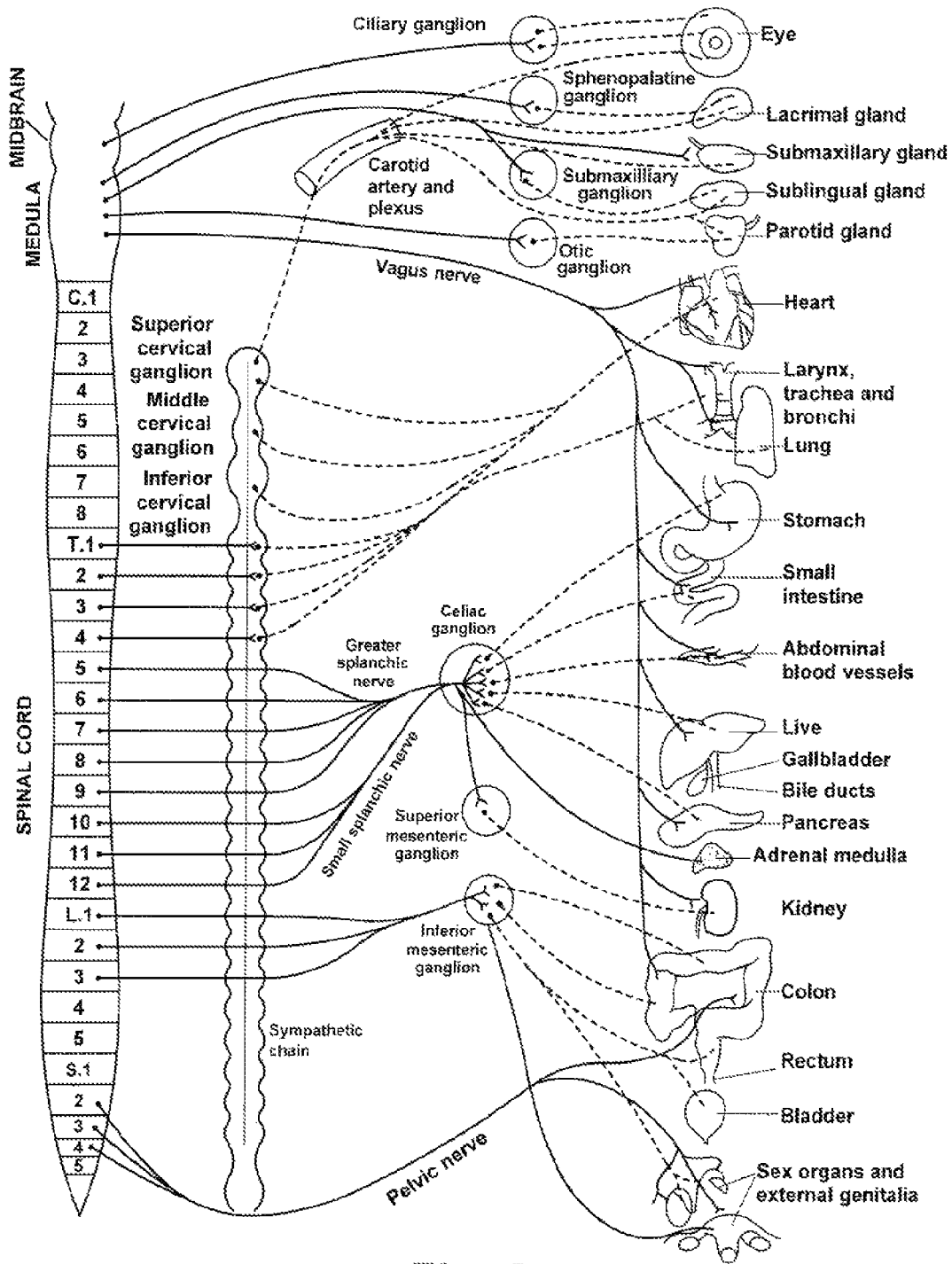
FIG. 2 is a schematic illustration of the autonomic nervous system showing the sympathetic division and the projections of the sympathetic division.

A brief discussion of the neurophysiology is provided to assist the reader with understanding the present invention. The autonomic nervous system is a subsystem of the human nervous system that controls involuntary actions of the smooth muscles (blood vessels and digestive system), the heart, and glands (FIG. 2). The autonomic nervous system is divided into the SNS 32 and the PNS. The SNS 32 generally prepares the body for action by increasing heart rate, increasing blood pressure, and increasing metabolism. The PNS prepares the body for rest by lowering heart rate, lowering blood pressure, and stimulating digestion.

Figure 3:
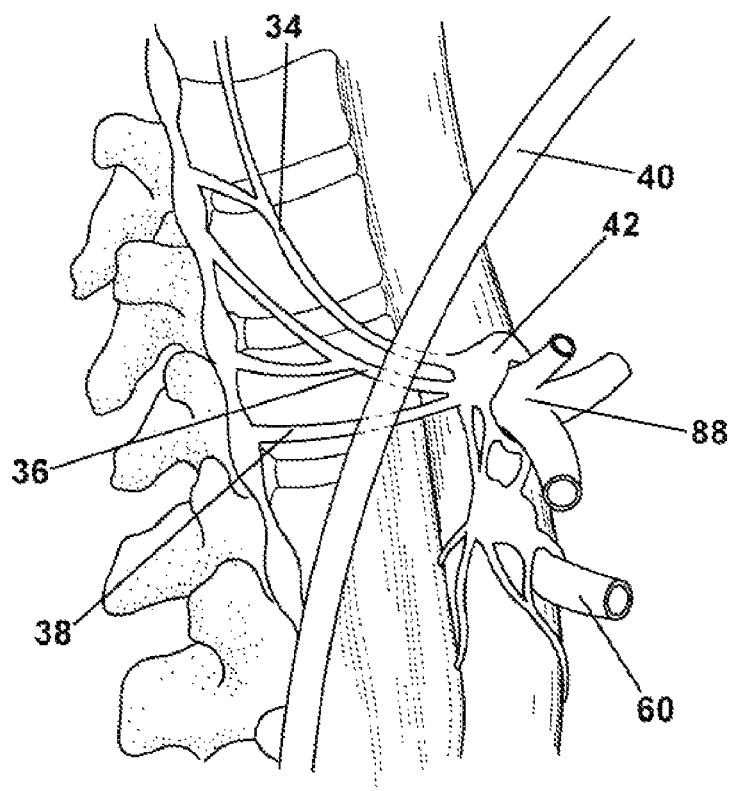
FIG. 3 is an elevation view of the splanchnic nerves and celiac ganglia.
Figure 5:
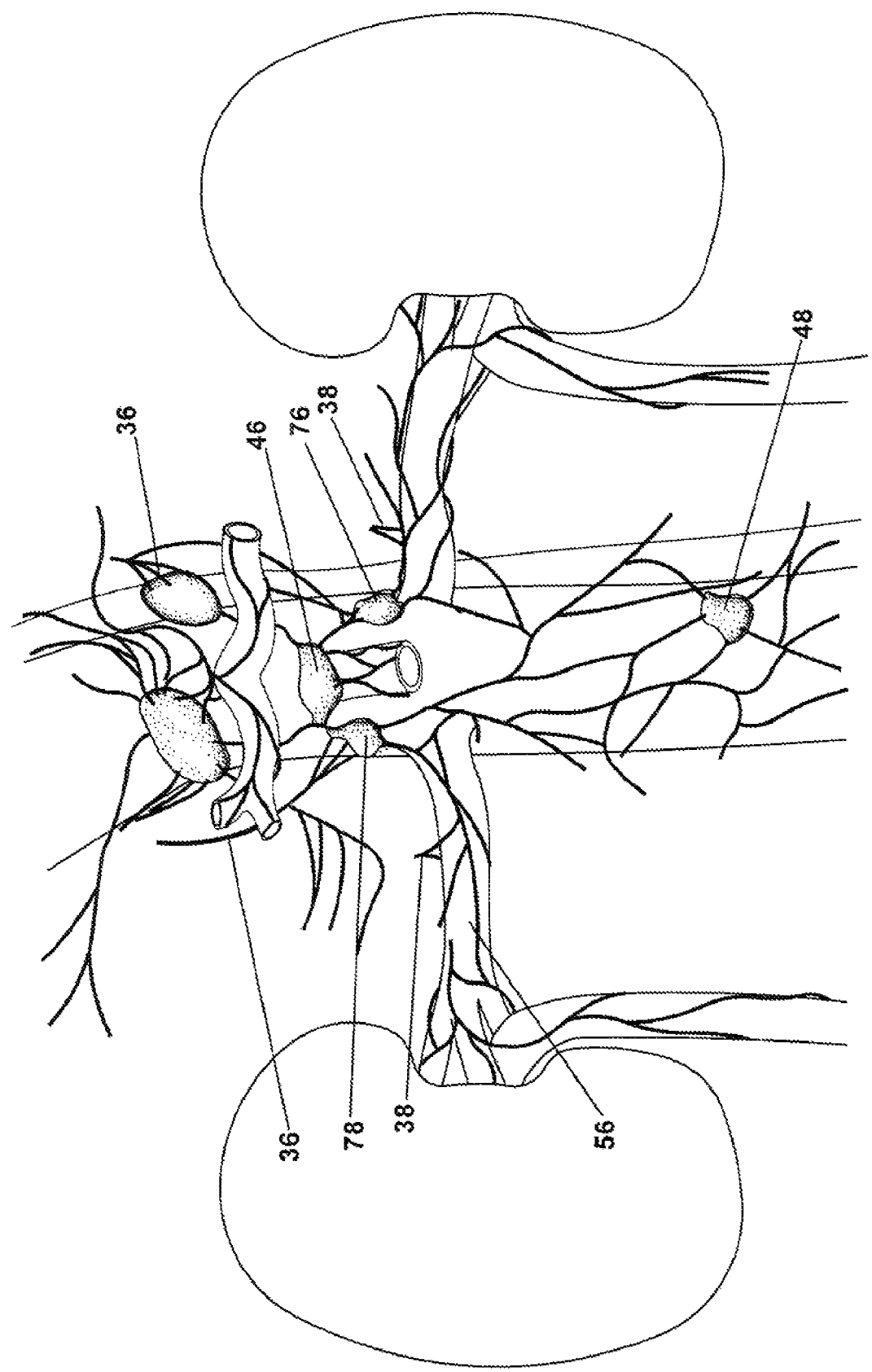
FIG. 5 is a schematic view illustrating sympathetic innervation of the renal anatomy.

Several large sympathetic nerves and ganglia are formed by the neurons of the SNS 32 (FIG. 3). The greater splanchnic nerve (GSN) 34 is formed by efferent sympathetic neurons exiting the spinal cord from thoracic vertebral segment numbers 4 or 5 (T4 or T5) through thoracic vertebral segment numbers 9 or 10 or 11 (T9, T10, or T11). The lesser splanchnic nerve (lesser SN) 36 is formed by preganglionic, sympathetic efferent fibers from T10 to T12. The least splanchnic nerve (least SN) 38 is formed by fibers from T12. The GSN 34 is typically present bilaterally in animals, including humans, with the other splanchnic nerves having a more variable pattern. The splanchnic nerves run along the anterior-lateral aspect of the vertebral bodies, pass out of the thorax, and enter the abdomen through the diaphragm 40. The splanchnic nerves run in proximity to the azygous veins (not shown). Once in the abdomen, neurons of the GSN 34 synapse with postganglionic neurons primarily in celiac ganglia 42. Some neurons of the GSN 34 pass through the celiac ganglia 42 and synapse in the adrenal medulla 44 (FIG. 5) (not shown in detail). Neurons of the lesser SN 36 (FIG. 3) and least SN 38 synapse with post-ganglionic neurons in the mesenteric ganglia, such as the superior mesenteric ganglion 46 and the inferior mesenteric ganglion 48 (FIG. 5).

Postganglionic neurons, arising from the celiac ganglia 42 (FIG. 3) that synapse with the GSN 34, innervate primarily the upper digestive system, including the stomach, pylorus, duodenum, pancreas, and liver. In addition, blood vessels and adipose tissue of the abdomen are innervated by neurons arising from the celiac ganglia 42 and GSN 34. Postganglionic neurons of the mesenteric ganglia, supplied by preganglionic neurons of the lesser and least splanchnic nerve 36 and 38, innervate primarily the lower intestine, colon, rectum, kidneys, bladder, and sexual organs, and the blood vessels that supply these organs and tissues.

FIG. 4 illustrates the renal vasculature 30, including the ureters 68 and 70. The left and right kidneys 50 and 52 are located lateral to the vertebral column between the last thoracic and third lumbar vertebrae on each side. The superior surface of the right kidney 52 is situated inferior to the superior surface of the left kidney 50. The position of the kidneys 50 and 52 in the abdominal cavity is maintained by the overlying peritoneum, contact with adjacent visceral organs, and supporting connective tissues. Each of the kidneys 50 and 52 is protected and stabilized by three concentric layers of connective tissue (i.e., the renal capsule, the adipose capsule, and the renal fascia).

The kidneys 50 and 52 receive 20-25% of the total cardiac output. In normal individuals, about 1200 mL of blood flows through the kidneys 50 and 52 each minute. Each of the kidneys 50 and 52 receives blood from left and right renal arteries 54 and 56, respectively, that originate along the lateral surface of the abdominal aorta 58 near the level of the superior mesenteric artery 60 (FIG. 3). For the purposes of the present invention and for ease of reference, the left and right renal arteries 54 and 56 may each be segmented into proximal 61, medial 63, and distal 65 portions (FIG. 4). As the renal arteries 54 and 56 enter the renal sinuses (not shown), they branch into the segmental arteries (not shown). The segmental arteries further divide into a series of interlobular arteries (not shown) that radiate outward, penetrating the renal capsule and extending through the renal columns (not shown) between the renal pyramids (not shown). The interlobular arteries supply blood to the arcuate arteries (not shown) that parallel the boundary between the cortex (not shown) and medulla (not shown) of the kidneys 50 and 52. Each arcuate artery gives rise to a number of interlobular arteries supplying portions of the adjacent renal lobe. Numerous afferent arterioles (not shown) branch from each interlobular artery to supply individual nephrons (not shown). From the nephrons, blood enters a network of venules (not shown) and small veins (not shown) that converge on the interlobular veins (not shown). In a mirror image of the arterial distribution, the interlobular veins deliver blood to arcuate veins (not shown) that empty into further interlobular veins. The interlobular veins merge to form the renal veins 62 and 64, which drain into the inferior vena cava 66.

FIG. 5 illustrates sympathetic innervation of the renal vasculature 30. The kidneys 50 and 52 are innervated by renal nerves 72. Most of the nerves 72 involved are sympathetic postganglionic fibers from the superior mesenteric ganglion 46. Renal nerves 72 enter each of the kidneys 50 and 52 at the hilum 74 and follow the branches of the renal arteries 54 and 56 to reach individual nephrons. Other renal ganglia, such as the celiac ganglia 42, the superior mesenteric ganglion 46, the left and right aorticorenal ganglia 76 and 78, and the inferior mesenteric ganglion 48 also innervate the renal vasculature 30. Known functions of sympathetic innervation include: (1) regulation of renal blood flow and pressure; (2) stimulation of renin release; and (3) direct stimulation of water and sodium ion reabsorption.

To address the problems of renal disease and diseases or conditions associated with renal disease, the present invention provides an apparatus 10 (FIG. 1) and method for renal neuromodulation. More particularly, the present invention provides an apparatus 10 and method for modulating renal function via the SNS, the PNS, or a combination thereof. Examples of renal function that can be modulated by the present invention include, but are not limited to, renal excretion, renal elimination, and homeostatic regulation.

Referring to FIG. 1, the apparatus 10 of the present invention comprises an expandable support member 12 for engaging a wall of a blood vessel and for modulating renal function. As used herein, the term "modulate" or "modulating" refers to causing a change in neuronal activity, chemistry, and/or metabolism without ablating or destroying nerve structure. The change can refer to an increase, decrease, or even a change in a pattern of neuronal activity. For example, efferent nerve activity and/or afferent nerve activity of the SNS, PNS, PNS and SNS, or somatic nervous system can be modulated by the present invention. The term may refer to either excitatory or inhibitory stimulation, or a combination thereof, and may be at least electrical, biological, magnetic, optical or chemical, or a combination of two or more of these. The term "modulate" can also be used to refer to a masking, altering, overriding, or restoring of neuronal activity. It will be appreciated that the same or different apparatus 10 can be used to modulate neuronal activity of a first nerve in one manner and the neuronal activity of a second nerve in a different manner.

As shown in FIG. 1, the expandable support member 12 includes oppositely disposed first and second end portions 24 and 26 and a main body portion 14 extending between the end portions. The structure of the expandable support member 12 may be a mesh, a zigzag wire, a spiral wire, an expandable stent, or other similar configuration that allows the expandable support member to be collapsed and expanded. The expandable support member 12 can be comprised of a material having a high modulus of elasticity, including, for example, cobalt-nickel alloys (e.g., Elgiloy), titanium, nickel-titanium alloys (e.g., Nitinol), cobalt-chromium alloys (e.g., Stellite), nickel-cobalt-chromium-molybdenum alloys (e.g., MP35N), graphite, ceramic, stainless steel, and hardened plastics. The expandable support member 12 may also be made of a radio-opaque material or include radio-opaque markers to facilitate fluoroscopic visualization.

The flexible and expandable properties of the expandable support member 12 facilitate percutaneous delivery of the expandable support member, while also allowing the expandable support member to conform to a portion of a blood vessel. An expanded configuration of the expandable support member 12 is shown in FIG. 1. In the expanded configuration, the expandable support member 12 has a circular cross-sectional shape for conforming to the circular cross-sectional shape of the blood vessel lumen. By conforming to the shape of the blood vessel lumen, the expanded configuration of the expandable support member 12 facilitates movement of the blood flow therethrough while also maintaining lumen patency.

Figure 13:
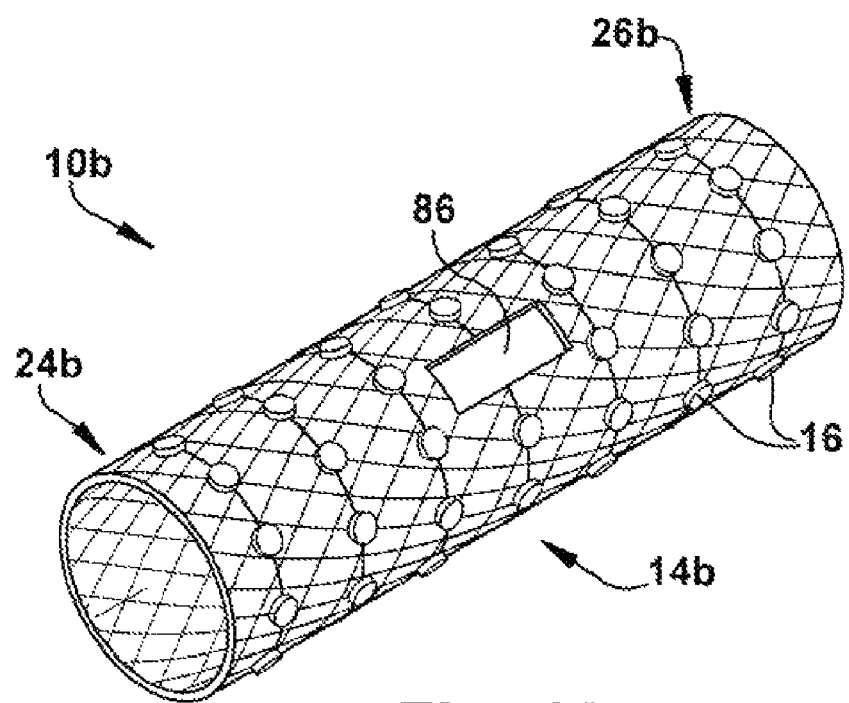
FIG. 13 is a perspective view showing another alternative embodiment of the apparatus shown in FIG. 1.

At least one constraining band 28 may be placed around the circumference of the expandable support member 12 to maintain the expandable support member in the collapsed configuration. As shown in FIG. 13, the constraining bands 28 may comprise sutures, for example, and may be placed around the circumference of the expandable support member 12 as needed. Removal of the constraining bands 28 allows the expandable support member 12 to self-expand and obtain the expanded configuration. Where the constraining bands 28 comprise sutures, for example, the sutures may be manually broken or, alternatively, broken by the radial force generated when the expandable support member 12 self-expands. It will be appreciated that the constraining bands 28 may comprise any other type of material capable of being selectively modified. For example, the constraining bands 28 may be made of a shape memory alloy, such as Nitinol, which can be selectively modified (i.e., expanded) by delivering energy (e.g., thermal energy) to allow the expandable support member 12 to obtain the expanded configuration.

The expandable support member 12 (FIG. 1) also includes at least one fenestration 20 and at least one branch member 22. As shown in FIG. 1, and more clearly shown in FIG. 10, the fenestrations 20 include a hole or opening disposed about the main body portion 14 of the expandable support member 12. FIG. 1 illustrates an expandable support member 12 having two fenestrations 20; however, it will be appreciated that the expandable support member may include any number of fenestrations disposed about the main body portion 14.

As shown in FIG. 1, the expandable support member 12 also includes two branch members 22. The branch members 22 are constructed in an identical or substantially identical fashion as the main body portion 14 of the expandable support member 12, and include first and second end portions 23 and 25. The first end portion 23 of each of the branch members 22 is anastomosed with the fenestrations 20 such that the lumen of each of the branch members is in fluid communication with the lumen of the main body portion 14. As described in more detail below, the first end portion 23 of each of the branch members 22 may be anastomosed with the fenestrations 20 using any one or combination of techniques known in the art. Means for anastomosing the first end portion 23 of each of the branch members 22 to the fenestrations include 20, but are not limited to, sutures, clips, staples, pins, adhesives, and the like. Although the expandable support member 12 of FIG. 1 is shown with two branch members 22, it should be appreciated that any number of branch members may be included with the expandable support member.

The expandable support member 12 also includes at least one electrode 16 for delivering an electric current to a desired location. As shown in FIG. 1, the electrodes 16 have a flat, disc-like shape and are radially disposed about the circumference of the expandable support member 12 in a multi-electrode array configuration. It will be appreciated, however, that the electrodes 16 may have any shape and size, including, for example, a triangular shape, a rectangular shape, an ovoid shape, and/or a band-like shape (e.g., a split band configuration), and are not limited to the shapes and sizes illustrated in FIG. 1. The electrodes 16 may be configured so that the expandable support member 12 has a unipolar construction (FIG. 6A) using the surround tissue as ground or, alternatively, a bipolar construction using leads connected to either end of the expandable support member (FIG. 7A). The electrodes 16 may be made of any material capable of conducting an electrical current, such as platinum, platinum-iridium, or the like.

Figure 9:
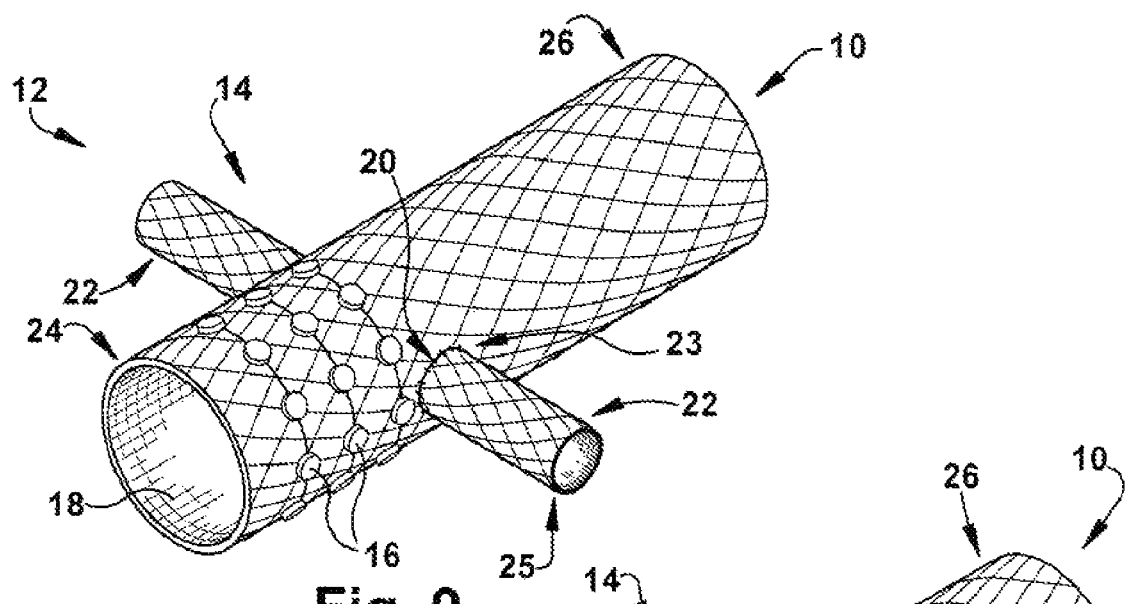
FIG. 9 is a perspective view showing an alternative embodiment of the apparatus in FIG. 1.
Figure 10:
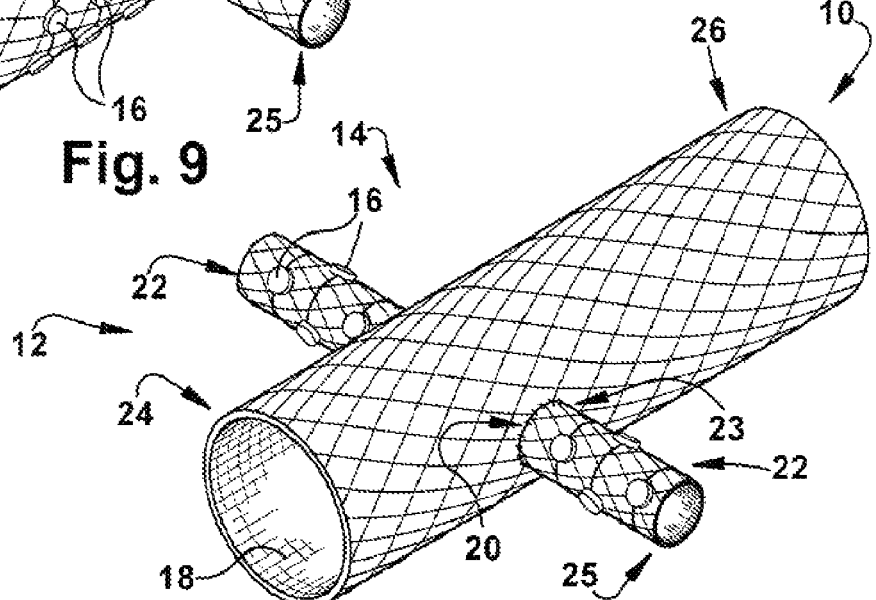
FIG. 10 is a perspective view showing another alternative embodiment of the apparatus in FIG. 1.

As shown in FIG. 1, the electrodes 16 can extend around only a portion or the entire circumference of the expandable support member 12 in a radial fashion. Alternatively, the electrodes 16 may extend around only a portion or the entire circumference of the expandable support member 12 in a sinusoidal or helical fashion (FIG. 7A). The entire length of the expandable support member 12 may be covered with the electrodes 16 or, alternatively, only a portion of the expandable support member, such as the first end portion 24 (FIG. 9), may be covered with the electrodes. Additionally, it will be appreciated that the electrodes 16 may extend around only the main body portion 14 or, alternatively, only around the branch members 22 (FIG. 10).

To facilitate focal delivery of electrical energy to a desired location, the electrodes 16 may wrap around the expandable support member 12 any number of times to establish a desired electrode contact and coverage. Additionally or optionally, the entire surface area of the electrodes 16 may be conductive or, alternatively, only a portion of the surface area of the electrodes may be conductive. By modifying the conductivity of the surface of the electrodes 16, the surface area of the electrodes that contact the blood vessel wall may be selectively modified to facilitate focal delivery of electrical energy to the desired location.

Electrical energy can be delivered to the electrodes 16 using a variety of internal, passive, or active energy sources 80 (FIGS. 6A-8B). The energy source 80 may include, for example, radio frequency (RF) energy, X-ray energy, microwave energy, acoustic or ultrasound energy such as focused ultrasound or high intensity focused ultrasound energy, light energy, electric field energy, magnetic field energy, piezoelectric, combinations of the same, or the like (see, e.g., U.S. patent application Ser. No. 12/016,115, the entirety of which is hereby incorporated by reference). Another example of an energy source 80 can include a magnetic powering mechanism (not shown) which may be worn as a belt or waistband.

Figure 6A:
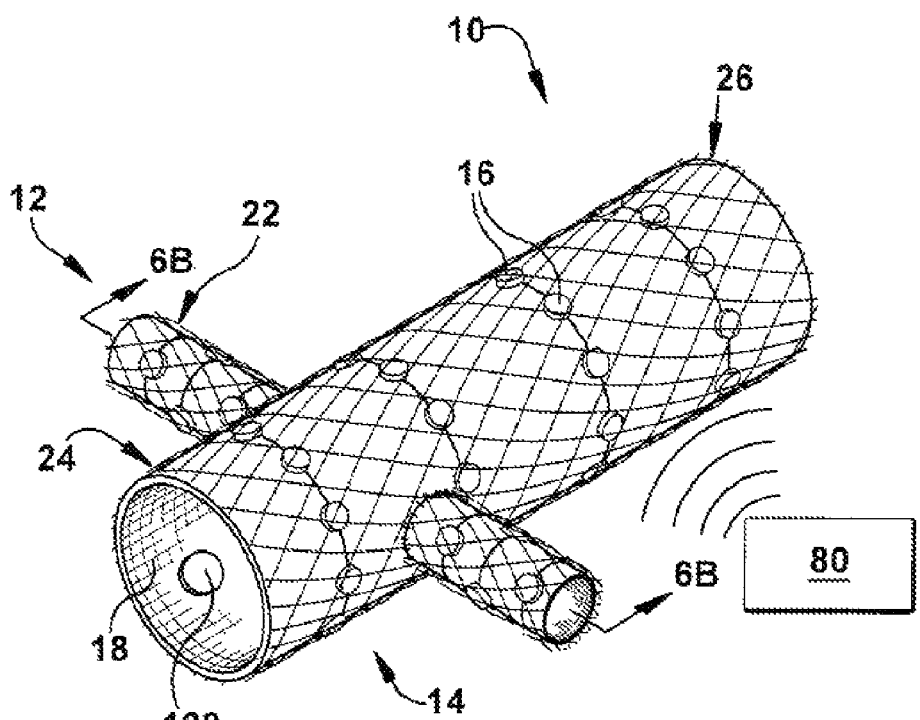
FIG. 6A is a perspective view showing the apparatus in FIG. 1 receiving electrical energy from a wireless energy delivery source.
Figure 6B:
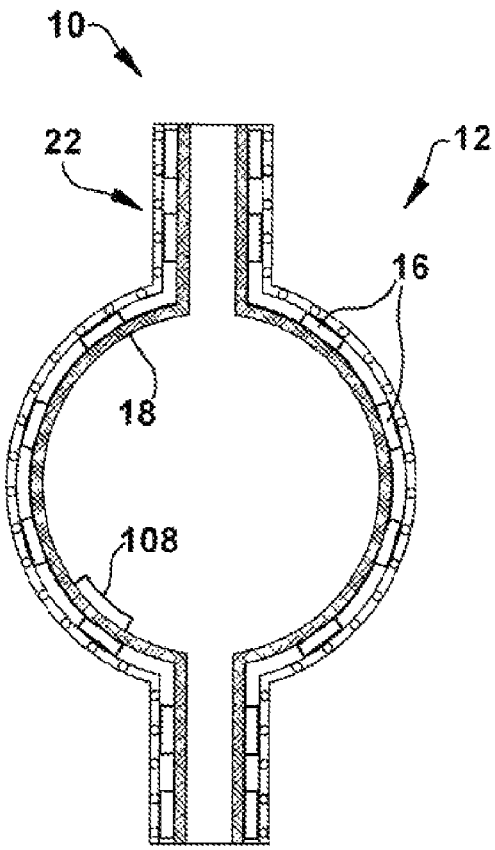
FIG. 6B is a schematic sectional view taken along line 6-6 in FIG. 6A.

As shown in FIG. 7A, an energy source 80 may be directly coupled or tethered to the apparatus 10 using an electrical lead 82. The electrical lead 82 may be disposed in an adjacent blood vessel, such as the inferior vena cava 66, and travel down the length of the inferior vena cava to a remote entry site (not shown). Alternatively, as shown in FIG. 8A, electrical energy may be supplied to the electrodes 16 via a turbine-like mechanism 84 operatively disposed in the lumen of the expandable support member 12. As blood flows through the lumen of the expandable support member 12, the turbine mechanism 84 generates electrical energy which may then be delivered to the electrodes 16. Further, the energy source 80 may be wirelessly coupled to the apparatus 10 as shown in FIG. 6A.

It will be appreciated that the energy source 80 can include a rechargeable battery (not shown) that is operably coupled to the apparatus 10. For example, an external charger (not shown) can be inductively coupled to a charging circuit (not shown) that is operably coupled to the apparatus 10 to recharge the battery. The external charger can include a charging coil energizable to create an electromagnetic field that in turn induces current in a corresponding coil within the charging circuit. The coil may be mounted to a waist pack, wearable skin-contacting/adhering patch, purse, backpack, or wheelchair cushion, for example, so that it can be carried by the patient in sufficient proximity to the charging circuit. Alternatively, the coil may be positioned within a pad positionable on a patient's mattress, allowing for charging of the battery while the patient rests.

Electrical energy can be delivered to the electrodes 16 continuously, periodically, episodically, or a combination thereof. For example, electrical energy can be delivered in a unipolar, bipolar, and/or multipolar sequence or, alternatively, via a sequential wave, charge-balanced biphasic square wave, sine wave, or any combination thereof. Electrical energy can be delivered to all the electrodes 16 at once or, alternatively, to only a select number of desired electrodes. The particular voltage, current, and frequency delivered to the electrodes 16 may be varied as needed. For example, electrical energy can be delivered to the electrodes 16 at a constant voltage (e.g., at about 0.1 v to about 25 v), at a constant current (e.g., at about 25 microamps to about 50 milliamps), at a constant frequency (e.g., at about 5 Hz to about 10,000 Hz), and at a constant pulse-width (e.g., at about 50 μsec to about 10,000 μsec).

Delivery of electrical energy to a select number of electrodes 16 may be accomplished via a controller (not shown), for example, operably attached to the apparatus 10. The controller may comprise an electrical device which operates like a router by selectively controlling delivery of electrical energy to the electrodes 16. For example, the controller may vary the frequency or frequencies of the electrical energy being delivered to the electrodes 16. By selectively controlling delivery of electrical energy to the electrodes 16, the controller can facilitate focal delivery of electrical energy to a desired location.

It should be appreciated that means other than electrical energy, such as chemical or biological means, may also be used for renal neuromodulation. For example, the apparatus 10 may include at least one pharmacological agent for eluting into the vascular tissue and/or blood stream. The pharmacological agent may be capable of preventing a variety of pathological conditions including, but not limited to, hypertension, hypotension, anemia, thrombosis, stenosis and inflammation. Accordingly, the pharmacological agent may include at least one of a diuretic agent, an anti-anemia agent, an anti-hypertensive, an anti-hypotensive agent, an anticoagulant, an antioxidant, a fibrinolytic, a steroid, an anti-apoptotic agent, and an anti-inflammatory agent. Another example of a pharmacological agent includes botulinum toxin (e.g., BOTOX).

Optionally or additionally, the pharmacological agent may be capable of treating or preventing other diseases or disease processes such as microbial infections. In these instances, the pharmacological agent may include an anti-microbial agent and/or a biological agent such as a cell, peptide, or nucleic acid. The pharmacological agent can be simply linked to the surface of the apparatus 10, embedded and released from within polymer materials, such as a polymer matrix, or surrounded by and released through a carrier.

Referring again to FIG. 1, the expandable support member 12 additionally comprises an insulative material 18 for isolating blood flow through the vessel from the electric current. More particularly, the insulative material 18 serves as an electrical insulator, separating electrical energy from blood flow and facilitating delivery of electrical energy to the vessel wall. The insulative material 18 is disposed radially inward of the electrodes 16 and extends along the entire length of the expandable support member 12. Alternatively, the insulative material 18 may be attached to select portions of the expandable support member 12, such as only the second end portion 26 and part of the main body portion 14. The insulative material 18 may be disposed between the electrodes 16 and the expandable support member 12 (FIG. 7B) disposed about the lumen of the expandable support member (FIGS. 6B and 8B), or, alternatively, extend the entire length of the expandable support member (not shown). The insulative material 18 generally has a low electrical conductivity and a non-thrombogenic surface. The insulative material 18 can include materials such as PTFE, ePTFE, silicone, silicone-based materials, and the like.

In addition to the insulative layer 18, at least a portion of the expandable support member 12 may optionally include a layer (not shown) of biocompatible material. The layer of biocompatible material may be synthetic such as DACRON (Invista, Wichita, Kans.), GORE-TEX (W. L. Gore & Associates, Flagstaff, Ariz.), woven velour, polyurethane, or heparin-coated fabric. Alternatively, the layer of biocompatible material may be a biological material such as bovine or equine pericardium, peritoneal tissue, an allograft, a homograft, patient graft, or a cell-seeded tissue. The biocompatible layer can cover either the luminal surface of the expandable support member 12, the non-luminal surface of the expandable support member, or can be wrapped around both the luminal and non-luminal surfaces. The biocompatible layer may be attached around the entire circumference of the expandable support member 12 or, alternatively, may be attached in pieces or interrupted sections to allow the expandable support member to more easily expand and contract.

The apparatus 10 can be part of an open- or closed-loop system. In an open-loop system, for example, a physician or subject may, at any time, manually or by the use of pumps, motorized elements, etc. adjust treatment parameters such as pulse amplitude, pulse width, pulse frequency, or duty cycle. Alternatively, in a closed-loop system, electrical parameters may be automatically adjusted in response to a sensed symptom or a related symptom indicative of the extent of the renal disease being treated. In a closed-loop feedback system, a sensor 108 (FIG. 6A) that senses a condition (e.g., a metabolic parameter of interest) of the body can be utilized. More detailed descriptions of sensors 108 that may be employed in a closed-loop system, as well as other examples of sensors and feedback control techniques that may be employed are disclosed in U.S. Pat. No. 5,716,377, the entirety of which is hereby incorporated by reference.

Although described in more detail below, it should be appreciated that incorporating the apparatus 10 as part of a closed-loop system can include placing the apparatus in a blood vessel adjacent a desired location, detecting a bodily activity associated with a renal disease, and then activating the apparatus to apply electric current to the desired location in response to the detected bodily activity. Such bodily activity can include any characteristic or function of the body, such as renal blood flow or renal volume, urine output, urine chemistry, urine osmolarity, plasma renin, plasma angiotensin, urine pH, specific gravity, urine protein content, urine blood content, urine ketone content, respiratory function (e.g., respiratory rate), body temperature, blood pressure, metabolic activity such as fluid glucose levels, hormone levels, enzyme or enzyme byproduct levels, and/or nitrogen, oxygen and/or carbon dioxide levels, body temperature, cerebral blood flow, pH levels (e.g., in blood, tissue, and other bodily fluids), galvanic skin responses (e.g., perspiration), electrocardiogram, muscle tone in the diaphragm and other muscles, electroencephalogram, nerve action potential, body movement, response to external stimulation, speech, motor activity, ocular activity, cognitive function, and the like.

It should be appreciated that an override mechanism (not shown) for overriding a closed-loop system can also be included as part of the present invention. For example, where a patient is diagnosed with congestive heart failure, the override mechanism could be used to override the closed-loop system and permit dieresis of the patient.

Figure 11:
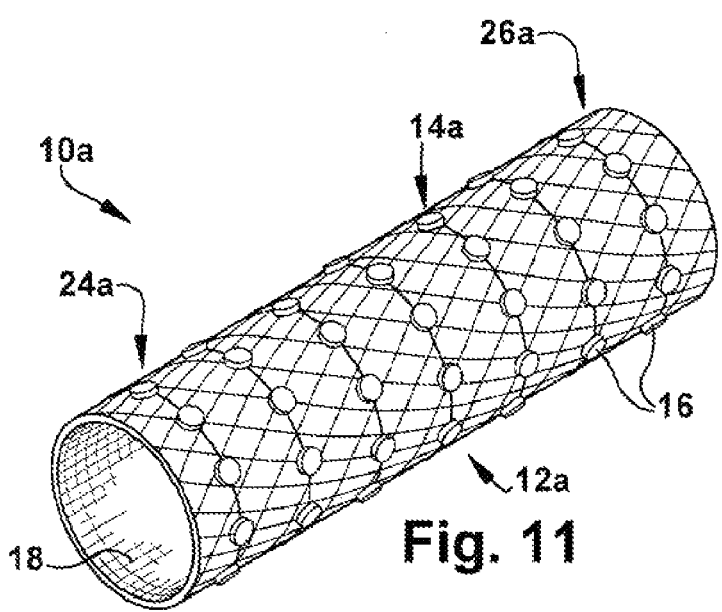
FIG. 11 is a perspective view showing another alternative embodiment of the apparatus shown in FIG. 1.

Another embodiment of the present invention is illustrated in FIG. 11. In FIG. 11, an apparatus $10_a$ for renal neuromodulation is provided. The apparatus $10_a$ is identical to the apparatus 10 illustrated in FIG. 1, except where as described below. In FIG. 11, structures that are identical as structures in FIG. 1 use the same reference numbers, whereas structures that are similar but not identical carry the suffix "a".

Figure 12:
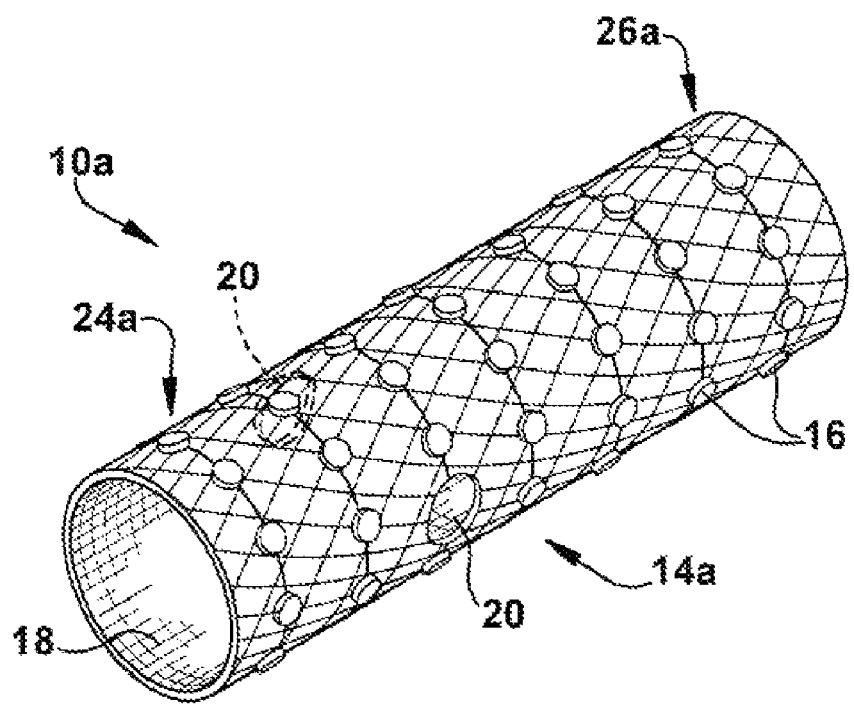
FIG. 12 is a perspective view showing an alternative embodiment of the apparatus shown in FIG. 11.

As shown in FIG. 11, the apparatus $10_a$ comprises an expandable support member $12_a$ having a main body portion $14_a$ for engaging a wall of a blood vessel proximate a renal vasculature 30. The expandable support member $12_a$ includes at least one electrode 16 arranged to selectively deliver electric current to a desired location where modulation of the SNS is effective to alter renal function. Additionally, the expandable support member $12_a$ includes an insulative material 18 attached to at least a portion of the main body portion $14_a$. As discussed above, the insulative material 18 is for isolating blood flow through the vessel from the electric current delivered by the electrodes 16. The expandable support member $12_a$ may also include at least one fenestration 20 as illustrated in FIG. 12.

Another embodiment of the present invention is illustrated in FIG. 13. In FIG. 13, an apparatus $10_b$ for renal neuromodulation is provided. The apparatus $10_b$ is identical to the apparatus $10_a$ illustrated in FIG. 11, except where as described below. In FIG. 13, structures that are identical as structures in FIG. 11 use the same reference numbers, whereas structures that are similar but not identical carry the suffix "b".

As shown in FIG. 13, the apparatus $10_b$ comprises an expandable support member $12_b$ having a main body portion $14_b$ for engaging a wall of a blood vessel proximate a renal vasculature 30. The expandable support member $12_b$ includes at least one electrode 16 arranged to selectively deliver electric current to a desired location where modulation of the SNS is effective to alter renal function. Additionally, the expandable support member $12_b$ includes at least one wireless module 86 capable of receiving electrical energy for delivery to the electrodes 16. It should be appreciated that the apparatus $10_b$ shown in FIG. 13 may include other components, such as fenestrations 20 and branch members 22.

The wireless module 86 may be operably coupled to the expandable support member $12_b$ as shown in FIG. 13. The wireless module 86 may comprise an electrical device which operates like a router by selectively controlling delivery of electrical energy to the electrodes 16. For example, the wireless module 86 may vary the frequency or frequencies of the electrical energy being delivered to the electrodes 16. By selectively controlling delivery of electrical energy to the electrodes 16, the wireless module 86 can facilitate focal delivery of electrical energy to a desired location. Alternatively, the wireless module 86 may passively distribute electrical energy to the electrodes 16.

To address the problems of renal disease and conditions associated with renal disease, the present invention provides a method for renal neuromodulation using a minimally invasive, laparoscopic, cystoscopic, uretoroscopic, open surgical, percutaneous, or endovascular approach. It should be appreciated, however, that a minimally invasive surgical approach may also be used. According to the present invention, an apparatus 10, or only a portion of an apparatus, is positioned substantially adjacent a desired location in a blood vessel. For purposes of illustration only, the present invention is described with reference to the apparatus 10 being positioned in the renal arteries 54 and 56 and in the abdominal aorta 58 proximate the renal arteries. It will be appreciated, however, that the apparatus 10 may additionally or optionally be placed at other desired locations, such as in the renal veins 62 and 64, the inferior vena cava 66 proximate the renal veins, the superior mesenteric artery 60, and/or the celiac artery 88 (FIG. 3).

Prior to use of the apparatus 10 (FIG. 1), the dimensions of the left and right renal arteries 54 and 56, as well as the dimension of the abdominal aorta 58 proximate the renal arteries will need to be determined. Various methods and devices for determining the dimensions of the abdominal aorta 58 and renal arteries 54 and 56 are known in the art and include, for example, computed tomography, magnetic resonance imaging, angiography and fluoroscopy. After determining the dimensions of the left and right renal arteries 54 and 56 and the abdominal aorta 58 proximate the renal arteries, an appropriately-sized apparatus 10 is chosen. The apparatus 10 is suitably sized, for example, so that the dimensions of the main body portion 14 of the expandable support member 12 in the expanded configuration correspond to the dimensions of the abdominal aorta 58 proximate the renal arteries 54 and 56. Additionally, the apparatus 10 is suitably sized so that dimensions of the branch members 22 in the expanded configuration correspond to the dimensions of the renal arteries 54 and 56.

Figure 14:
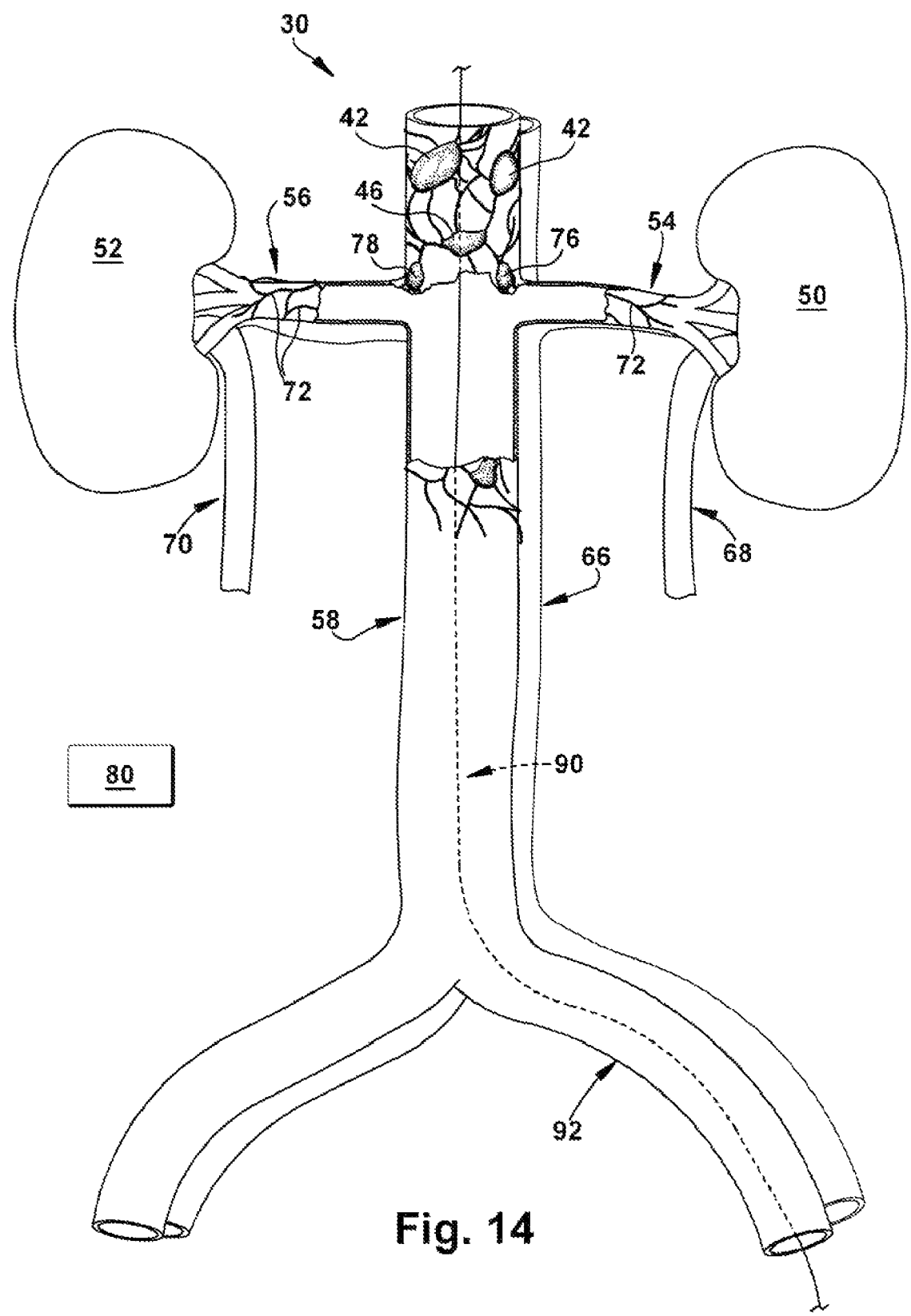
FIG. 14 is a schematic view showing a guidewire extending through a femoral artery into the abdominal aorta.

Percutaneous placement of the apparatus 10 starts by accessing a bodily vessel with a delivery device. For instance, a first guidewire 90 (FIG. 14) may be introduced into the vasculature via a vascular opening or incision (not shown). Vascular access may be through a peripheral arterial access site (not shown), such as a left femoral artery 92. The first guidewire 90 is inserted through the incision into the left femoral artery 92 in an antegrade direction. Alternatively, the first guidewire 90 may be inserted into the brachlocephalic artery (not shown) from an incision in the left subclavian artery (not shown) or left brachial artery (not shown) in a retrograde direction, or in a retrograde direction through the right subclavian artery (not shown), and then advanced toward the abdominal aorta 58. The first guidewire 90 is then urged into the abdominal aorta 58 proximate the renal arteries 54 and 56 as shown in FIG. 14.

Figure 15:
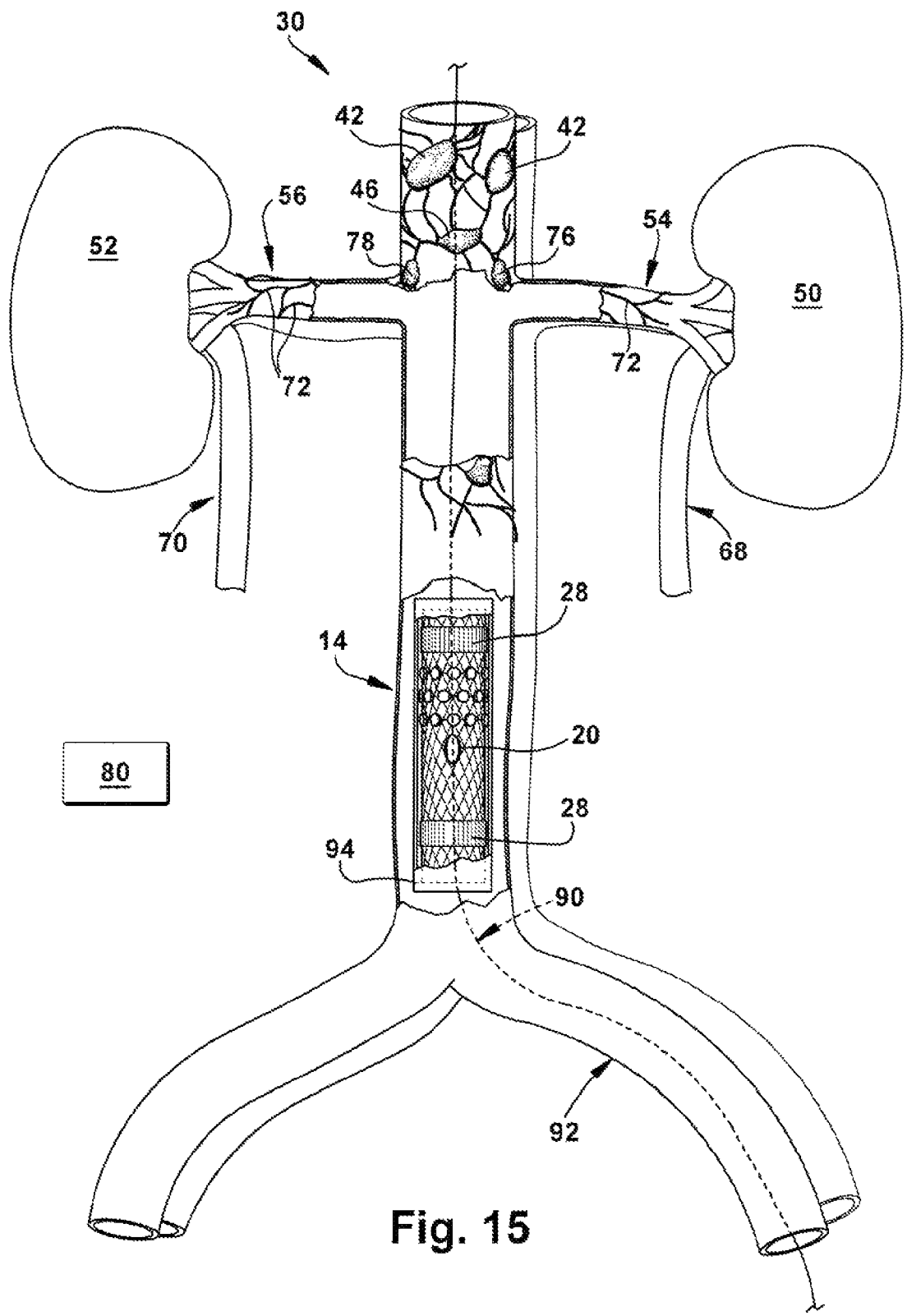
FIG. 15 is a schematic view showing the apparatus of FIG. 12 being delivered to the abdominal aorta proximate the renal vasculature.

Next, the main body portion 14 of the expandable support member 12 is placed in a first delivery catheter 94 in a collapsed configuration and securely attached to a proximal end (not shown) of the first guidewire 90. The first delivery catheter 94 is then advanced over the first guidewire 90 as shown in FIG. 15. The first delivery catheter 94 is advanced until the first delivery catheter is suitably positioned in the abdominal aorta 58 proximate the renal arteries 54 and 56. In particular, the main body portion 14 is positioned such that each of the fenestrations 20 is adjacent the ostium of each of the left and right renal arteries 54 and 56. Additionally, the main body portion 14 is positioned such that at least a portion of the main body portion is positioned substantially adjacent a desired target. For example, a portion of the main body portion 14 having a focal arrangement of electrodes 16 is positioned substantially adjacent the superior mesenteric ganglion 46 (FIG. 16).

Once the main body portion 14 of the expandable support member 12 is appropriately positioned in the abdominal aorta 58 proximate the renal arteries 54 and 56, the first delivery catheter 94 is removed and the constraining bands 28 are progressively released (i.e., broken) by the radial force generated by the self-expanding main body portion. It should be appreciated that the expandable support member 12 may also be expanded via other means, such as an expandable balloon (not shown). When all of the constraining bands 28 have been released, the main body portion 14 obtains the expanded configuration and is securely positioned in the abdominal aorta 58 proximate the renal arteries 54 and 56. With the main body portion 14 securely positioned in the abdominal aorta 58, the first guidewire 90 is then removed from the vasculature.

Figure 16:
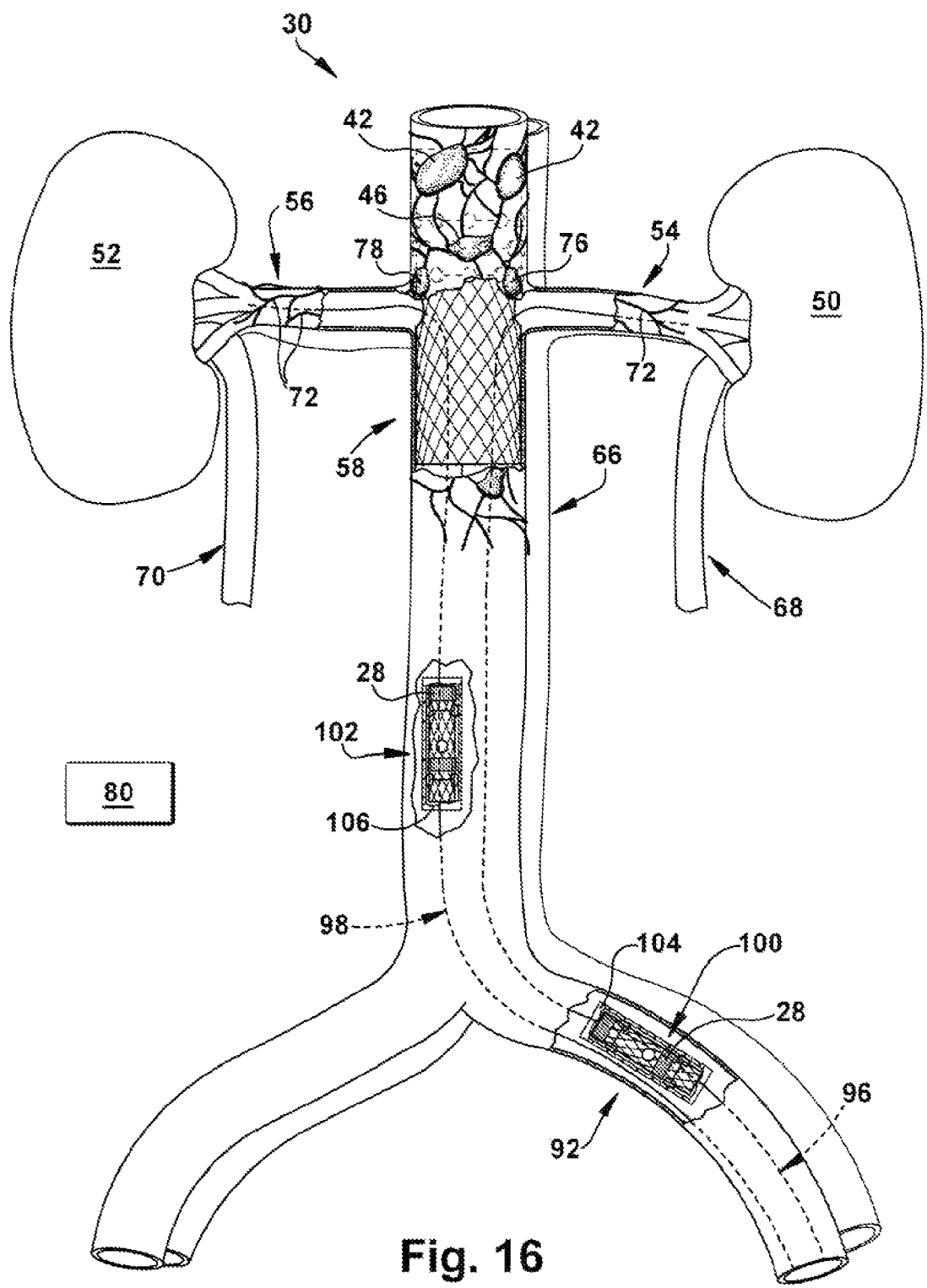
FIG. 16 is a schematic view showing branch members being delivered to the abdominal aorta proximate the renal vasculature.

As shown in FIG. 16, second and third guidewires 96 and 98 are then inserted into the left femoral artery 92 and advanced in an antegrade direction. The second and third guidewires 96 and 98 are advanced so that the second and third guidewires respectively extend into the left and right renal arteries 54 and 56. Next, first and second branch members 100 and 102 are respectively placed in second and third delivery catheters 104 and 106 in a collapsed configuration and securely attached to the proximal ends (not shown) of the second and third guidewires 96 and 98. The second and third delivery catheters 104 and 106 are then respectively advanced in an antegrade direction over the second and third guidewires 96 and 98 as shown in FIG. 16. The second and third delivery catheters 104 and 106 are next respectively advanced through the lumen of the main body portion 14, through the fenestrations 20, and into the left and right renal arteries 54 and 56.

Figure 17:
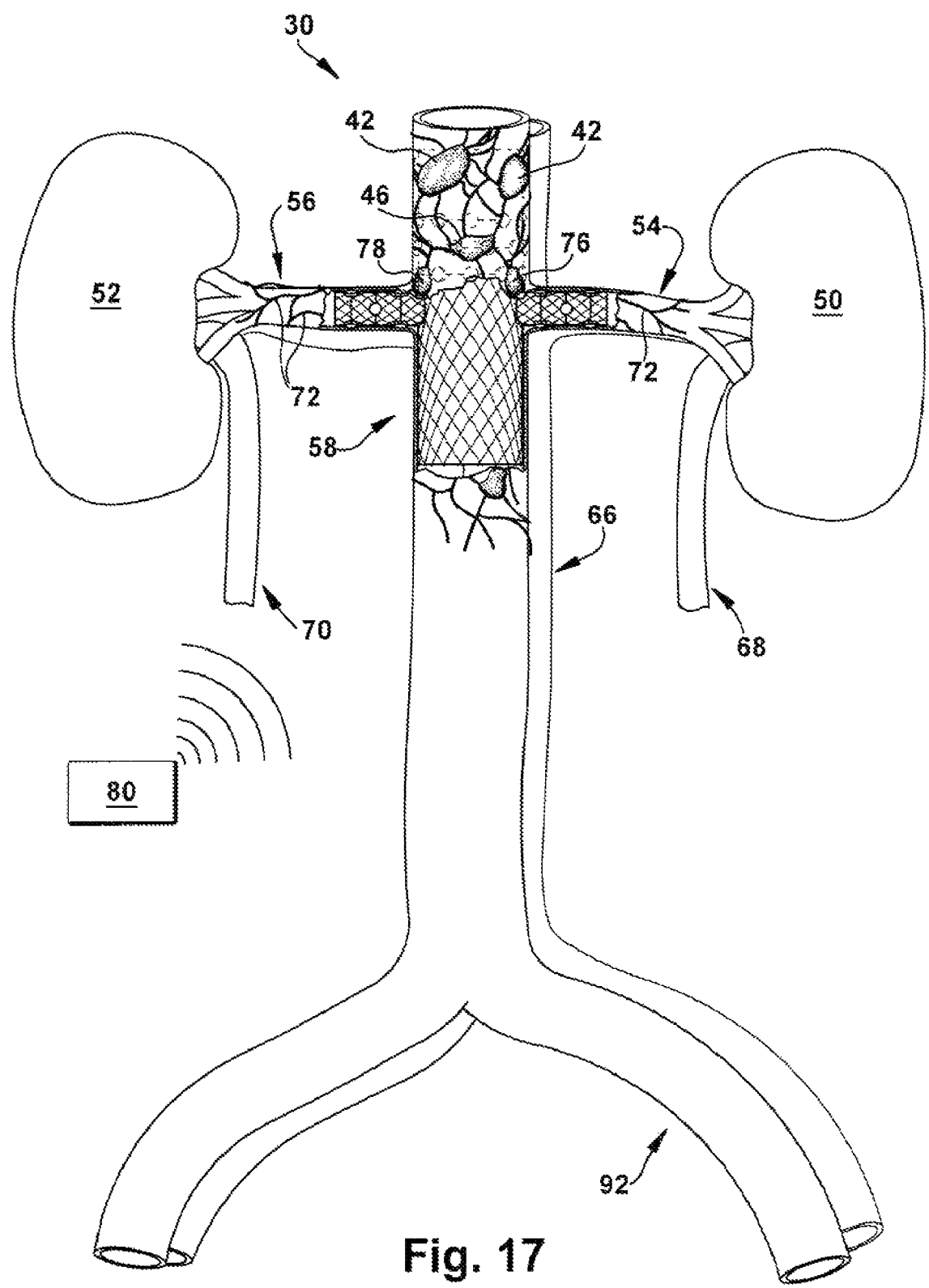
FIG. 17 is a schematic view showing the apparatus of FIG. 1 implanted in the renal anatomy.

After delivery to the left and right renal arteries 54 and 56, the first and second branch members 100 and 102 are positioned such that each branch member is substantially adjacent a desired location. As shown in FIG. 17, for example, the first and second branch members 100 and 102 are positioned so that the electrodes 16 of each of the branch members is located in the proximal portion 61 of each of the left and right renal arteries 54 and 56. Consequently, the electrodes 16 of each of the first and second branch members 100 and 102 are positioned substantially adjacent the left and right aorticorenal ganglion 76 and 78, respectively. It should be appreciated that the arrangement of the electrodes 16 on each the branch members 22 may be varied to selectively deliver electrical energy to different portions of the renal arteries 54 and 56. For example, the electrodes 16 of the branch members 22 may be arranged so that electrical energy can be delivered to the medial 63 and/or distal portion 65 of each of the renal arteries 54 and 56 and thus deliver electrical energy to select renal nerves 72.

Once the first and second branch members 100 and 102 are appropriately positioned, the second and third delivery catheters 104 and 106 are removed and the constraining bands 28 are progressively released (i.e., broken) by the radial force generated by the self-expanding branch members. When all of the constraining bands 28 have been released, the first and second branch members 100 and 102 each obtain the expanded configuration and are securely positioned in the left and right renal arteries 54 and 56, respectively.

With the first and second branch members 100 and 102 respectively positioned in the left and right renal arteries 54 and 56, the first end portion 23 of each of the branch members is anastomosed with the corresponding fenestration 20 using, for example, sutures or ties (FIG. 17). The first and second branch members 100 and 102 are securely anastomosed with the fenestrations 20 such that the lumen of each of the branch members is in fluid communication with the lumen of the main body portion 14. It will be appreciated that other methods known in the art may be used to securely anastomose the first and second branch members 100 and 102 with the fenestrations 20. Examples of such methods are disclosed in U.S.

Pat. No. 6,827,735 and U.S. Pat. Pub. No. 2006/0247761, each of which is hereby incorporated by reference in its entirety.

After the first and second branch members 100 and 102 are positioned in the left and right arteries 54 and 56, respectively, the second and third guidewires 96 and 98 are removed from the vasculature. Next, electrical energy, such as RF energy, may be delivered to the apparatus 10 via a wirelessly coupled energy source 80 as shown in FIG. 17. As electrical energy is delivered to the apparatus 10, the electrodes 16 conduct the electrical energy to the vascular wall at the desired locations and thereby cause nerves associated with the desired locations to fire action potentials. Electrical energy delivered to the electrodes 16 on the main body portion 14, for example, causes the superior mesenteric ganglion 46 to fire action potentials. The action potentials are then relayed to efferent nerve fibers, which emanate from the superior mesenteric ganglion 46 and innervate the efferent and afferent arterioles (not shown) of the kidneys 50 and 52.

Depending upon the desired neuromodulatory effect, electrical energy may be delivered to the electrodes 16 so that the efferent and/or afferent arterioles are either activated, inhibited, or alternately activated and inhibited. For example, electrical energy may be delivered to the electrodes 16 to cause constriction of the efferent arterioles which, in turn, may increase renal filtration and urine production. Alternatively, electrical energy may be delivered to the electrodes 16 to cause constriction of the afferent arterioles and thereby reduce renal filtration and urine production. Further, electrical energy may be delivered to the electrodes 16 to cause constriction of the efferent arterioles while alternately reducing or inhibiting constriction of the afferent arterioles and, thus, increase renal filtration and urine production.

Additionally or optionally, electrical energy may be delivered to the electrodes 16 to modulate the renin-angiotensin-aldosterone system (RAAS). The RAAS regulates renal vasomotor activity, maintains optimal salt and water homeostasis, and controls tissue growth in the kidneys 50 and 52. RAAS function is controlled by the SNS and, in particular, SNS modulation of juxtaglomerular apparatus (JGA) cells. The JGA cells form part of the wall of the afferent arterioles and secrete renin in response to various stimuli. In the kidneys 50 and 52, renin converts angiotensin to angiotensin I, which is then converted to angiotensin II by angiotensin converting enzyme in the lungs (not shown). Angiotensin II in turn causes water retention by two mechanisms: directly acting on tubules (not shown) to promote sodium and water reabsorption; and indirectly stimulating aldosterone secretion in the adrenal cortex (not shown).

Pathologic consequences can result from overactivity of the RAAS, thus involving the RAAS in the pathophysiology of kidney disease. An activated RAAS promotes both systemic and glomerular capillary hypertension, which can induce hemodynamic injury to the vascular endothelium and glomerulus. Dysfunction of the RAAS is also implicated in congestive heart failure and chronic renal failure.

Accordingly, electrical energy may be delivered to the electrodes 16 to effect a change in the RAAS. As described below, delivering electrical energy to the electrodes 16 may in turn alter renal function and thus be useful for treating conditions related to or caused by renal dysfunction, such as hypertension, for example. Electrical energy can be delivered to the electrodes 16 to decrease or inhibit nerve conduction from the superior mesenteric ganglion 46 to select efferent nerve fibers. A decrease or inhibition of nerve conduction from the superior mesenteric ganglion 46 will decrease or inhibit activity of the JGA cells and, thus, decrease or inhibit renin production. As a result of a decrease in renin production, the RAAS will be altered and thereby lead to a decrease in blood pressure. It will be appreciated that modulating the SNS, and thus altering the RAAS, may be useful for treating not only hypertension, but also any number of other renal diseases or conditions associated therewith, such as congestive heart failure, chronic renal failure, and the like.

During delivery of electrical energy to the apparatus 10, at least one metabolic parameter of interest, such as blood chemistry, blood-sodium content, or urine chemistry may be measured via a sensor 108 (FIG. 6A). The sensor 108 may comprise any suitable device that measures or monitors a parameter indicative of the need to modify the activity of the apparatus 10. For example, the sensor 108 may comprise a physiologic transducer or gauge that measures blood pressure (systolic, diastolic, average or pulse pressure), blood volumetric flow rate, blood flow velocity, blood pH, $O_2$ or $CO_2$ content, nitrogen content, hemodynamic factors (e.g., renin/angiotensin, blood glucose, inflammatory mediators, tissue factors, etc.), mixed venous oxygen saturation ($SVO_2$), vasoactivity, nerve activity, and tissue activity or composition.

The sensor 108 may be separate from the apparatus 10 or combined therewith (FIG. 6A). The sensor 108 may also be positioned in/on a blood vessel and/or organ, such as in a chamber of the heart (not shown), or in/on a major artery, such as the abdominal aorta 58, such that the parameter of interest may be readily ascertained. It will be appreciated that the sensor 108 can also be used to detect various urine-associated parameters of interest, such as urine output, urine chemistry, urine osmolarity, urine pH, urine protein content, urine blood content, and urine ketone content. Additionally, it will be appreciated that the sensor 108 may be used to detect a metabolic parameter of interest associated with the pulmonary system. Examples of such pulmonary parameters of interest, as well as sensors that may be used to detect the parameters are disclosed in U.S. patent application Ser. No. 12/016,115.

An electrical stimulus regimen comprising a desired temporal and spatial distribution of electrical energy to a desired location may be selected to promote long-term efficacy of the present invention. To treat a chronic renal disease, for example, it may be useful to deliver continuous electrical energy to the apparatus 10. Alternatively, where an acute renal disease is being treated, it may useful to temporarily deliver electrical energy to the apparatus 10. It is theorized that uninterrupted or otherwise unchanging delivery of electrical energy to a desired location may result in associated nerves becoming less responsive over time, thereby diminishing the long-term effectiveness of the therapy. Therefore, the electrical stimulus regimen may be selected to activate, deactivate, or otherwise modulate the apparatus 10 in such a way that therapeutic efficacy is maintained for a desired period of time.

In addition to maintaining therapeutic efficacy over time, the electrical stimulus regimen may be selected to reduce the power requirement/consumption of the present invention. For example, the electrical stimulus regimen may dictate that the apparatus 10 be initially activated at a relatively higher energy and/or power level, and then subsequently activated at a relatively lower energy and/or power level. The first level attains the desired initial therapeutic effect, and the second (lower) level sustains the desired therapeutic effect long term. By reducing the energy and/or power levels after the desired therapeutic effect is initially attained, the energy required or consumed by the apparatus 10 is also reduced long-term.

It should be appreciated that unwanted collateral stimulation of adjacent tissues may be limited by creating localized cells or electrical fields (i.e., by limiting the electrical field beyond a desired location). Localized cells may be created by, for example, spacing the electrodes 16 very close together or biasing the electrical field with conductors (not shown) and/or magnetic fields. For example, electrical fields may be localized or shaped by using electrodes 16 with different geometries, by using one or more multiple electrodes, and/or by modifying the frequency, pulse-width, voltage, stimulation waveforms, paired pulses, sequential pulses, and/or combinations thereof.

Figure 18:
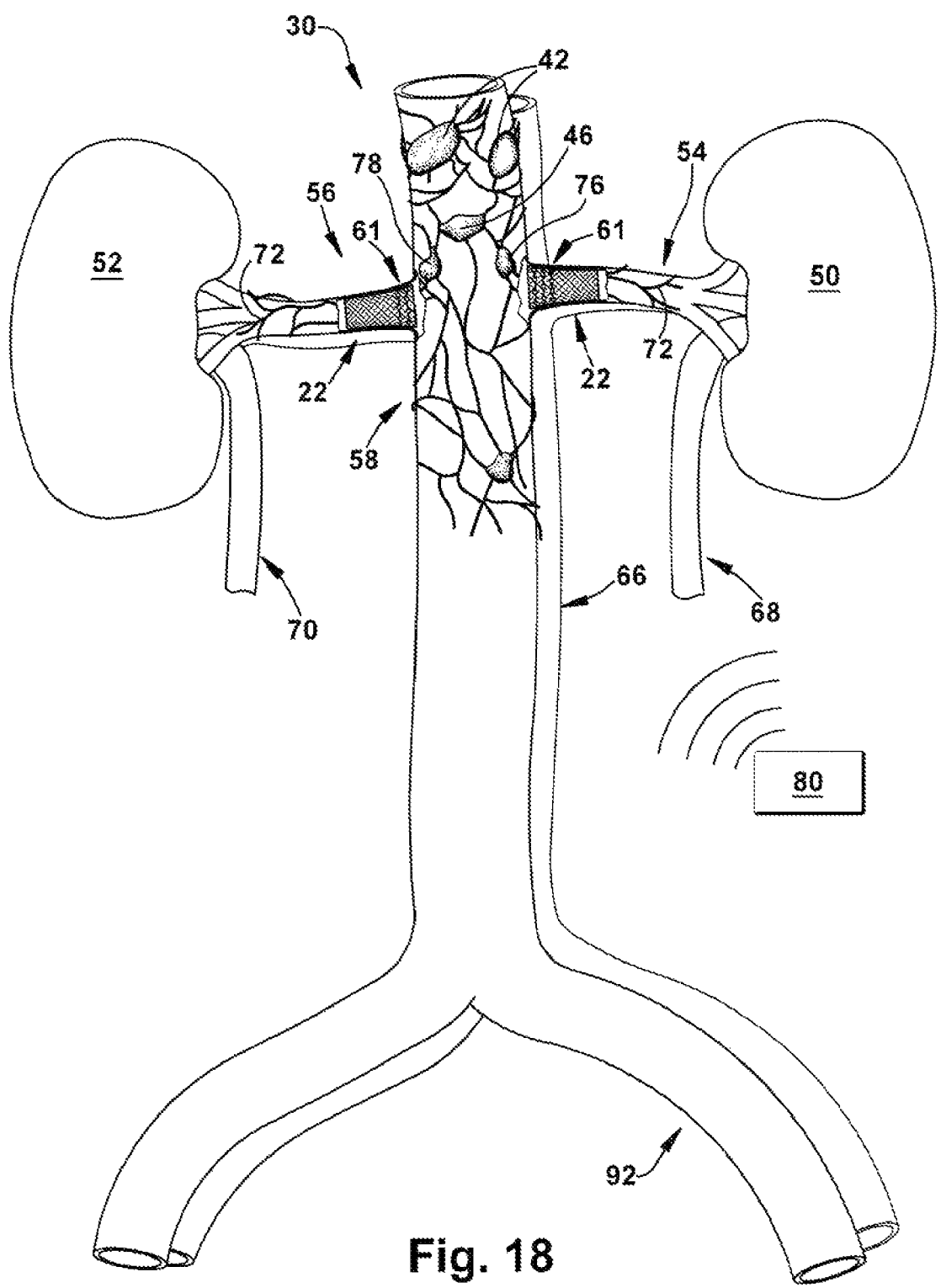
FIG. 18 is a schematic view showing branch members implanted in the renal vasculature.

It should also be appreciated that more than one apparatus 10 may be used to modulate the SNS. For example, it may be desirable to modulate the celiac ganglia 42 via an electrical field by placing one apparatus 10 in the abdominal aorta 58 proximate the renal arteries 54 and 56 and another apparatus in the inferior vena cava 66 proximate the renal veins 62 and 64. With this arrangement, the electrical field created between the two apparatus 10 may be used to modulate SNS activity at the celiac ganglia 42. As shown in FIG. 18, it will be further appreciated that two branch members 22 can be respectively placed in the left and right renal arteries 54 and 56.

Although the above method is described in terms of modulating the SNS to treat a renal disease, it will be appreciated that the method of the present invention may also include modulation of the PNS or both the SNS and the PNS. Components of the PNS that can be modulated according to the present invention include, but are not limited to, descending components of the vagus nerve, pre-ganglionic PNS fibers traveling with SNS fibers in the celiac plexus, the aorticorenal ganglion, and ascending PNS inputs into the kidney(s) (e.g., from the sacral plexus and the pelvic splanchnic nerves with inputs from the inferior hypogastric plexus, the superior hypogastric plexus, and the intermesenteric plexus).

Figure 19:
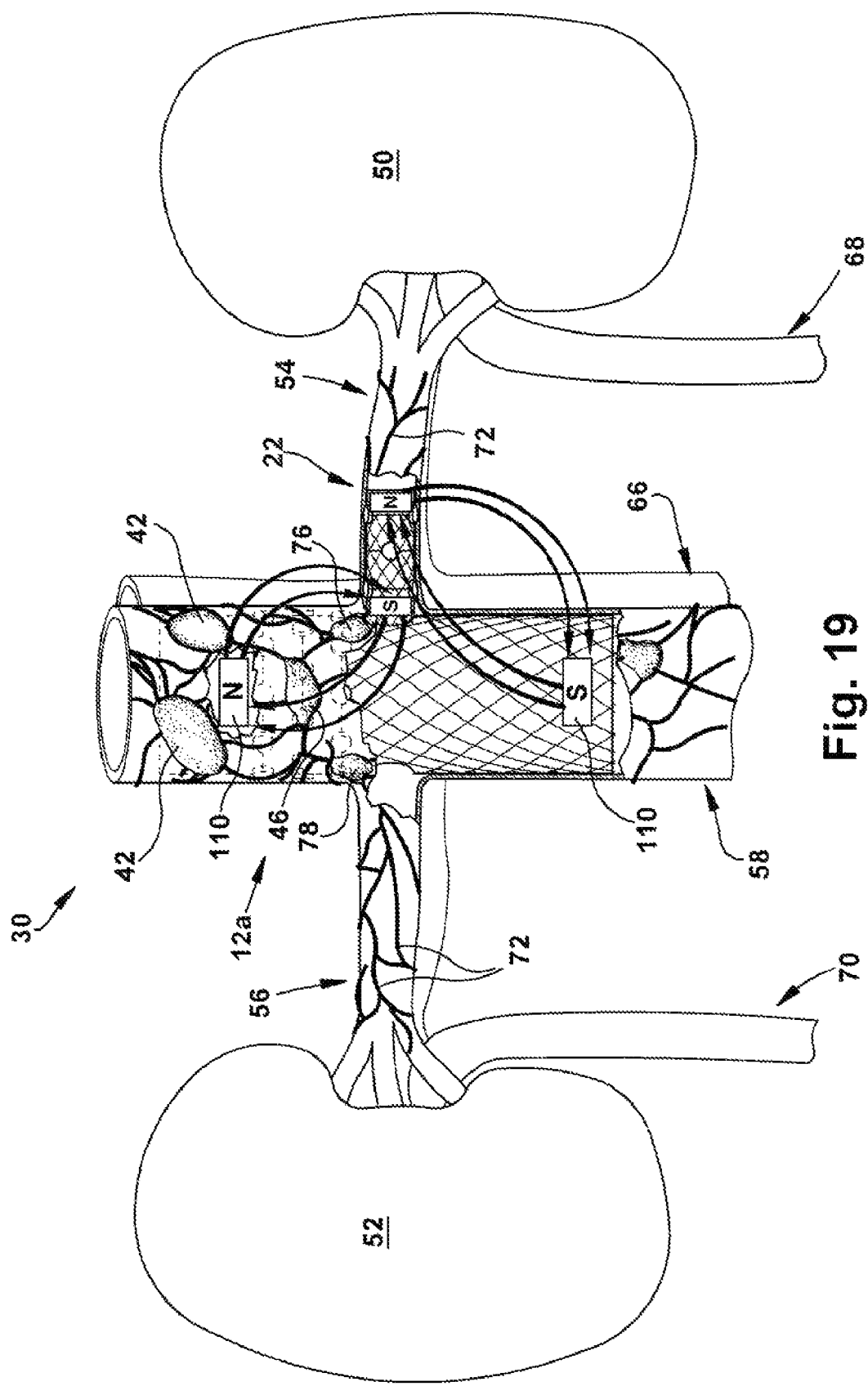
FIG. 19 is a schematic view showing an alternative embodiment of the apparatus in FIG. 1 implanted in the renal anatomy.

In another embodiment of the present invention, a method for renal neuromodulation is provided. As shown in FIG. 19, the method includes implanting an expandable support member $12_a$ and a branch member 22 at first and second desired locations, respectively, so that at least a portion of each of the expandable support member and the branch member are positioned substantially adjacent the first and second desired locations. As shown in FIG. 19, the first desired location includes the abdominal aorta 58 proximate the renal arteries 54 and 56, and the second desired location includes the left renal artery. The expandable support member $12_a$ may be identically constructed as the expandable support member in FIG. 12, and the branch member 22 may be identically constructed as the branch members in FIG. 1, except where as described below.

As shown in FIG. 19, at least one magnetic member 110 may be securely attached to each of the expandable support member $12_a$ and the branch member 22. The magnetic member 110 may be made of any one or combination of known electromagnetic materials including, for example, iron, NdFeB, SmCO and Alnico. The magnetic member 110 may be securely attached to each of the expandable support member $12_a$ and the branch member 22 using any suitable means known in the art including, for example, soldering, staples, clips, sutures, and/or adhesives. The magnetic member 110 may be attached to each of the expandable support member $12_a$ and the branch member 22 at any desired location, such as at the first and second end portions 24 and 26 of the expandable support member and the first and second end portions 23 and 25 of the branch member. The magnetic member 110 may have any suitable shape or configuration including, for example, a circular shape, an ovoid shape, a square-like shape, and/or a rectangular shape. Alternatively or additionally, the magnetic member 110 may have a ring-like shape to completely encircle the expandable support member 12 and/or the branch member 22.

The expandable support member $12_a$ and the branch member 22 may be implanted at the first and second desired locations, respectively, using a minimally invasive, percutaneous, or endovascular approach as described above. The expandable support member $12_a$ and the branch member 22 may be respectively implanted in an arterial and venous vessel, in first and second arterial vessels, and/or in first and second venous vessels. As shown in FIG. 19, for example, the expandable support member $12_a$ and the branch member 22 may be respectively implanted in an abdominal aorta 58 proximate the renal arteries 54 and 56 and a left renal artery 54 using a percutaneous approach (as described above).

After the expandable support member $12_a$ and the branch member 22 are securely positioned at the first and second desired locations, an electromagnetic force may be generated between the magnetic members 110 connected to each of the expandable support member and the branch member. As indicted by the directional lines in FIG. 19, the magnetic members 110 are polarized upon placement and consequently generate an electric current between one another. The electric current may be distributed across the electrodes 16 of the expandable support member $12_a$ and the branch member 22 and then delivered to the first and second desired locations. By adjusting the size, number, and composition of the magnetic members 110, in addition to the position of the expandable support member $12_a$ and the branch member 22, the magnitude and direction of the electric current may be varied as needed.

In another embodiment of the present invention, a direct approach for renal neuromodulation is provided. By "direct" it is meant that an apparatus $10_a$ similar or identical to the apparatus of FIG. 11 can be placed on or near at least one nerve capable of effecting a change in the SNS, the PNS, the SNS and the PNS, or the somatic nervous system to alter renal function. A variety of surgical approaches may be used to directly modulate renal function. Examples of such surgical approaches include, but are not limited to, open surgical approaches, laparoscopic approaches, and percutaneous approaches.

Figure 20:
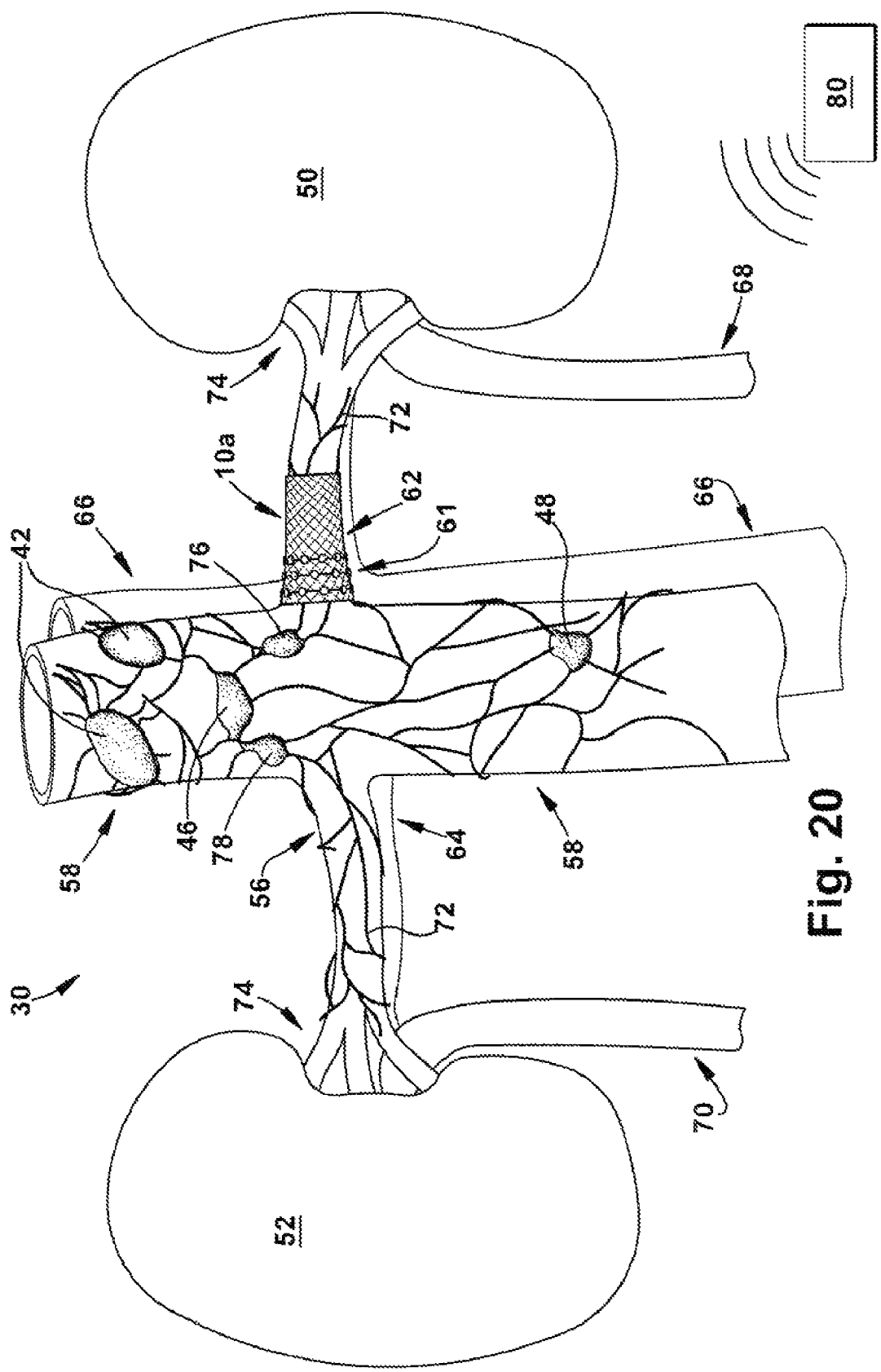
FIG. 20 is a schematic view showing an alternative embodiment of the apparatus in FIG. 1 placed extravascularly about a left renal artery.

Using laparoscopic surgery, for example, an apparatus $10_a$ similar or identical to the apparatus of FIG. 11 may be placed in a cuff-like manner around a desired extravascular location, such as the proximal portion of the left renal artery 54 (FIG. 20). Electrical energy may then be delivered to the electrodes 16 of the apparatus $10_a$, thereby modulating efferent nerve fibers emanating from the left aorticorenal ganglion 76 and thus altering renal function.

It will be appreciated that the apparatus $10_a$ may be placed at other desired locations to directly modulation renal function. For example, the apparatus $10_a$ may be placed at or near the cervical-thoracic segments of the sympathetic ganglia, including both pre- and post-ganglionic ganglia. Additionally or alternatively, the apparatus $10_a$ may be placed at or near the renal capsule, the adipose capsule, or the renal fascia to directly modulate renal function.

From the above description of the invention, those skilled in the art will perceive improvements, changes and modifications. Such improvements, changes, and modifications are within the skill of the art and are intended to be covered by the appended claims.

Having described the invention, we claim:

1. An apparatus for renal neuromodulation, said apparatus comprising:
   an expandable support member having a main body portion for engaging a wall of a blood vessel proximate a renal vasculature, said expandable support member including a lumen defined by an inner circumferential surface and an outer circumferential surface, said lumen extending between oppositely disposed first and second end portions of said expandable support member;

at least one electrode connected with said main body portion, said at least one electrode arranged to selectively deliver electric current to a desired location where modulation of the sympathetic nervous system (SNS) is effective to alter renal function; and an insulative material attached to at least a portion of said expandable support member, said insulative material extending the entire longitudinal length between said first and second end portions of said expandable support member, said insulative material extending circumferentially about the entirety of said inner circumferential surface of said expandable support member, said insulative material for isolating blood flow through the vessel from the electric current delivered by said at least one electrode.

2. The apparatus of claim 1, wherein modulation of the parasympathetic nervous system (PNS) is effective to alter renal function.

3. The apparatus of claim 1, wherein modulation of the PNS and the SNS is effective to alter renal function.

4. The apparatus of claim 1, where said expandable support member further includes at least one fenestration.

5. The apparatus of claim 1, wherein said expandable support member further includes at least one branch member for engaging a wall of a blood vessel in the renal vasculature, said at least one branch member comprising an expandable support member including first and second end portions and at least one electrode arranged to selectively deliver electric current to a desired location where modulation of the SNS is effective to alter renal function, said first end portion being anastomosed with said at least one fenestration.

6. The apparatus of claim 1, wherein said insulative material is disposed radially inward of said at least one electrode.

7. The apparatus of claim 6, wherein said expandable support member is disposed radially inward of said insulative material.

8. The apparatus of claim 6, wherein said insulative material is disposed radially inward of said expandable support member.

9. The apparatus of claim 6, wherein said at least one electrode is disposed radially inward of said expandable support member.

10. The apparatus of claim 1, wherein the at least one electrode is arranged to deliver a focal electric current to the desired location.

11. The apparatus of claim 1, wherein at least one magnetic member for generating an electromagnetic field is securely attached to said expandable support member.

12. The apparatus of claim 1, wherein said expandable support member further includes at least one pharmacological agent for chemically modulating the SNS.

13. The apparatus of claim 1, wherein said expandable support member further includes at least one biological agent for biologically modulating the SNS.

14. The apparatus of claim 1, wherein at least one sensor for measuring at least one metabolic parameter of interest is securely attached to said expandable support member.

15. The apparatus of claim 14, wherein said at least one sensor is positioned in or on a blood vessel.

16. The apparatus of claim 14, wherein said at least one sensor is positioned in or on an organ.

17. An apparatus for renal neuromodulation, said apparatus comprising:

an expandable support member for engaging a wall of a blood vessel proximate a renal vasculature, said expandable support member including a main body portion having at least one fenestration and at least one branch member for engaging a wall of a blood vessel in the renal vasculature, said at least one branch member comprising an expandable support member having first and second end portions, said expandable support member of said at least one branch member including a lumen that extends between said first and second end portions, said first end portion being anastomosed with said at least one fenestration;

at least one electrode connected with said expandable support member, said at least one electrode being arranged to selectively deliver electric current to a desired location where modulation of the sympathetic nervous system (SNS) is effective to alter renal function; and an insulative material attached to at least a portion of said expandable support member, said insulative material for isolating blood flow through the vessel from the electric current delivered by said at least one electrode.

18. The apparatus of claim 17, wherein modulation of the parasympathetic nervous system (PNS) is effective to alter renal function.

19. The apparatus of claim 17, wherein modulation of the PNS and the SNS is effective to alter renal function.

20. The apparatus of claim 17, wherein said at least one electrode is connected to each of said main body portion and said at least one branch member.

21. The apparatus of claim 17, wherein said at least one electrode is connected to said main body portion.

22. The apparatus of claim 17, wherein said at least one electrode is connected to said at least one branch member.

23. The apparatus of claim 17, wherein said insulative material is disposed radially inward of said at least one electrode.

24. The apparatus of claim 17, wherein said expandable support member is disposed radially inward of said insulative material.

25. The apparatus of claim 17, wherein said insulative material is disposed radially inward of said expandable support member.

26. The apparatus of claim 17, wherein said at least one electrode is disposed radially inward of said expandable support member.

27. The apparatus of claim 17, wherein said insulative material extends the entire length of said expandable support member.

28. The apparatus of claim 17, wherein the at least one electrode is arranged to deliver a focal electric current to the desired location.

29. The apparatus of claim 17, wherein at least one magnetic member for generating an electromagnetic field is securely attached to said expandable support member.

30. The apparatus of claim 17, wherein said expandable support member further includes at least one pharmacological agent for chemically modulating the SNS.

31. The apparatus of claim 17, wherein said expandable support member further includes at least one biological agent for biologically modulating the SNS.

32. The apparatus of claim 17, wherein at least one sensor for measuring at least one metabolic parameter of interest is securely attached to said expandable support member.

33. The apparatus of claim 32, wherein said at least one sensor is positioned in or on a blood vessel.

34. The apparatus of claim 32, wherein said at least one sensor is positioned in or on an organ.

35. An apparatus for renal neuromodulation, said apparatus comprising:
   an expandable support member having a main body portion for engaging a wall of a blood vessel proximate a renal vasculature, said expandable support member including a main body portion having at least one fenestration and at least one branch member for engaging a wall of a blood vessel in the renal vasculature, said at least one branch member comprising an expandable support member having first and second end portions, said expandable support member of said at least one branch member having a lumen extending between said first and second end portions, said first end portion being anastomosed with said at least one fenestration;
   at least one electrode connected with said expandable support member, said at least one electrode arranged to selectively deliver electric current to a desired location where modulation of the sympathetic nervous system (SNS) is effective to alter renal function; and
   at least one wireless module capable of receiving electrical energy for delivery to said at least one electrode.

36. The apparatus of claim 35, wherein modulation of the parasympathetic nervous system (PNS) is effective to alter renal function.

37. The apparatus of claim 35, wherein modulation of the PNS and the SNS is effective to alter renal function.

38. The apparatus of claim 35, wherein said expandable support member further includes an insulative material attached to at least a portion of said main body portion, said insulative material for isolating blood flow through the vessel from the electric current delivered by said at least one electrode.

39. The apparatus of claim 35, wherein said expandable support member further includes at least one fenestration.

40. The apparatus of claim 35, wherein said expandable support member further includes at least one branch member for engaging a wall of a blood vessel in the renal vasculature, said at least one branch member including first and second end portions and at least one electrode arranged to selectively deliver electric current to a desired location where modulation of the SNS is effective to alter renal function, said first end portion being anastomosed with said at least one fenestration.

41. The apparatus of claim 40, wherein said insulative material is disposed radially inward of said at least one electrode.

42. The apparatus of claim 40, wherein said expandable support member is disposed radially inward of said insulative material.

43. The apparatus of claim 40, wherein said insulative material is disposed radially inward of said expandable support member.

44. The apparatus of claim 35, wherein said at least one electrode is disposed radially inward of said expandable support member.

45. The apparatus of claim 35, wherein said insulative material extends the entire length of said expandable support member.

46. The apparatus of claim 35, wherein the at least one electrode is arranged to deliver a focal electric current to the desired location.

47. The apparatus of claim 35, wherein at least one magnetic member for generating an electromagnetic field is securely attached to said expandable support member.

48. The apparatus of claim 35, wherein said expandable support member further includes at least one pharmacological agent for chemically modulating the SNS.

49. The apparatus of claim 35, wherein said expandable support member further includes at least one biological agent for biologically modulating the SNS.

50. The apparatus of claim 35, wherein at least one sensor for measuring at least one metabolic parameter of interest is securely attached to said expandable support member.

51. The apparatus of claim 50, wherein said at least one sensor is positioned in or on a blood vessel.

52. The apparatus of claim 50, wherein said at least one sensor is positioned in or on an organ.

53. A method for renal neuromodulation, said method comprising the steps of:
   providing an expandable support member having a main body portion for engaging a wall of a blood vessel proximate a renal vasculature, the expandable support member including a lumen defined by an inner circumferential surface and an outer circumferential surface, the lumen extending between oppositely disposed first and second end portions of the expandable support member, at least one electrode connected with the main body portion arranged to selectively deliver electric current to a desired location, and an insulative material attached to at least a portion of the expandable support member, the insulative material extending the entire longitudinal length between the first and second end portions of the expandable support member, the insulative material extending circumferentially about the entirety of said inner circumferential surface of said expandable support member, the insulative material for isolating blood flow through the vessel from the electric current delivered by the at least one electrode;
   implanting the main body portion intravascularly so that the main body portion is proximate a renal vasculature and at least one electrode is positioned substantially adjacent a desired location where modulation of the sympathetic nervous system (SNS) is effective to alter renal function; and
   delivering electric current to the at least one electrode to effect a change in the SNS.

54. The method of claim 53, wherein said step of implanting the main body portion intravascularly includes positioning the at least one electrode substantially adjacent a desired location where modulation of the PNS and the SNS is effective to alter renal function.

55. The method of claim 53, wherein said step of implanting the main body portion intravascularly includes positioning the at least one electrode substantially adjacent a desired location where modulation of the parasympathetic nervous system (PNS) is effective to alter renal function.

56. The method of claim 53, wherein the change in the SNS includes a change in neurohormonal activation.

57. The method of claim 53, wherein said step of implanting the main body portion further includes positioning at least a portion of the main body portion substantially adjacent a desired location in an aortic arterial wall.

58. The method of claim 53, wherein said step of implanting the main body portion further includes positioning at least a portion of the main body portion substantially adjacent a desired location in a vena cava venous wall.

59. The method of claim 53, wherein the change in the SNS is chemically induced by at least one pharmacological agent associated with the expandable support member.

60. The method of claim 53, wherein the change in the SNS is biologically induced by at least one biological agent associated with the expandable support member.

61. The method of claim 53, wherein delivery of electric current to the at least one electrode modulates the level of rennin.

62. The method of claim 53, wherein delivery of electric current to the at least one electrode modulates at least one of urine production and blood pressure.

63. The method of claim 53, wherein delivery of electric current to the at least one electrode modulates vasoconstriction or blood vessel tone.

64. The method of claim 53, wherein delivery of electric current to the at least one electrode modulates efferent neuronal activity.

65. The method of claim 53, wherein delivery of electric current to the at least one electrode modulates afferent neuronal activity.

66. The method of claim 53, wherein delivery of electric current to the at least one electrode modulates both efferent and afferent neuronal activity.

67. A method for renal neuromodulation, said method comprising the steps of:
providing an expandable support member for engaging a wall of a blood vessel proximate a renal vasculature, the expandable support member including a main body portion having at least one fenestration and at least one branch member having first and second end portions, the first end portion being anastomosed with the at least one fenestration, at least one electrode connected with the expandable support member arranged to selectively deliver electric current to a desired location, and an insulative material attached to at least a portion of the expandable support member for isolating blood flow through the vessel from the electric current delivered by the at least one electrode;
implanting the main body portion intravascularly so that the main body portion is proximate a renal vasculature and at least one electrode is positioned substantially adjacent a desired location where modulation of the sympathetic nervous system (SNS) is effective to alter renal function;
deploying the at least one branch member such that the at least one branch member is positioned in the renal vasculature and at least one electrode is positioned substantially adjacent a desired location where modulation of the SNS is possible, the at least one branch member comprising an expandable support member having first and second end portions and a lumen that extends between the first and second end portions; and
delivering electric current to one or both of the at least one electrode to effect a change in the SNS.

68. The method of claim 67, wherein said step of delivering electric current to one or both of the at least one electrode effects a change in the parasympathetic nervous system (PNS).

69. The method of claim 67, wherein said step of delivering electric current to one or both of the at least one electrode effects a change in the PNS and the SNS.

70. The method of claim 67, wherein said step of deploying the at least one branch member further comprises anastomosing the first end portion of the at least one branch member with the at least one fenestration.

71. The method of claim 67, wherein the change in the SNS includes a change in neurohormonal activation.

72. The method of claim 67, wherein said step of implanting the main body portion further includes positioning at least a portion of the main body portion substantially adjacent a desired location in an aortic arterial wall.

73. The method of claim 67, wherein said step of implanting the main body portion further includes positioning at least a portion of the main body portion substantially adjacent a desired location in a vena cava venous wall.

74. The method of claim 67, wherein said step of deploying the at least one branch member further includes positioning at least a portion of the at least one branch member substantially adjacent a desired location in a renal arterial wall.

75. The method of claim 67, wherein said step of deploying the at least one branch member further includes positioning at least a portion of the at least one branch member substantially adjacent a desired location in a renal venous wall.

76. The method of claim 67, wherein the change in the SNS is chemically induced by at least one pharmacological agent associated with the expandable support member.

77. The method of claim 67, wherein the change in the SNS is biologically induced by at least one biological agent associated with the expandable support member.

78. The method of claim 67, wherein delivery of electric current to the at least one electrode modulates the level of renin.

79. The method of claim 67, wherein delivery of electric current to the at least one electrode modulates at least one of urine production and blood pressure.

80. The method of claim 67, wherein delivery of electric current to the at least one electrode modulates vasoconstriction or blood vessel tone.

81. The method of claim 67, wherein delivery of electric current to the at least one electrode modulates efferent neuronal activity.

82. The method of claim 67, wherein delivery of electric current to the at least one electrode modulates afferent neuronal activity.

83. The method of claim 67, wherein delivery of electric current to the at least one electrode modulates both efferent and afferent neuronal activity.

* * * * *